(12) United States Patent
Wasmuth et al.

(10) Patent No.: US 10,150,779 B2
(45) Date of Patent: Dec. 11, 2018

(54) ALDOSE REDUCTASE INHIBITORS AND METHODS OF USE THEREOF

(71) Applicant: THE TRUSTEES OF COLUMBIA UNIVERSITY IN THE CITY OF NEW YORK, New York, NY (US)

(72) Inventors: Andrew Wasmuth, Brooklyn, NY (US); Donald W. Landry, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/961,288

(22) Filed: Apr. 24, 2018

(65) Prior Publication Data

US 2018/0237451 A1    Aug. 23, 2018

Related U.S. Application Data

(63) Continuation of application No. PCT/US2017/038505, filed on Jun. 21, 2017.

(60) Provisional application No. 62/352,784, filed on Jun. 21, 2016.

(51) Int. Cl.
| | | |
|---|---|---|
| *C07D 495/04* | (2006.01) | |
| *A61P 9/10* | (2006.01) | |
| *A61P 25/02* | (2006.01) | |
| *A61P 13/12* | (2006.01) | |
| *A61P 17/00* | (2006.01) | |

(52) U.S. Cl.
CPC ............. *C07D 495/04* (2013.01); *A61P 9/10* (2018.01); *A61P 13/12* (2018.01); *A61P 17/00* (2018.01); *A61P 25/02* (2018.01)

(58) Field of Classification Search
CPC .................................................. C07D 495/04
See application file for complete search history.

(56) References Cited

U.S. PATENT DOCUMENTS

| | | | | |
|---|---|---|---|---|
| 4,868,301 A | * | 9/1989 | Mylari | C07D 237/32 544/237 |
| 4,939,140 A | | 7/1990 | Larson et al. | |
| 4,954,629 A | * | 9/1990 | Mylari | C07D 231/56 544/234 |
| 4,996,204 A | | 2/1991 | Mylari et al. | |
| 5,155,259 A | | 10/1992 | Suzuki et al. | |
| 5,304,557 A | | 4/1994 | Mylari | |
| 5,677,342 A | | 10/1997 | Malamas et al. | |
| 5,728,704 A | * | 3/1998 | Mylari | A61K 31/505 514/256 |
| 6,159,976 A | | 10/2000 | Lambert et al. | |
| 6,570,013 B2 | | 5/2003 | Mylari | |
| 6,579,879 B2 | | 6/2003 | Mylari | |
| 6,849,629 B2 | | 2/2005 | Mylari | |
| 7,572,910 B2 | | 8/2009 | Mylari | |
| 8,916,563 B2 | | 12/2014 | Wasmuth et al. | |
| 9,650,383 B2 | | 5/2017 | Wasmuth et al. | |
| 2006/0293265 A1 | | 12/2006 | Srivastava et al. | |
| 2006/0293371 A1 | | 12/2006 | Kamiyama | |
| 2013/0225592 A1 | | 8/2013 | Wasmuth et al. | |
| 2015/0072989 A1 | | 3/2015 | Wasmuth et al. | |
| 2017/0216291 A1 | | 8/2017 | Wasmuth et al. | |
| 2017/0216292 A1 | | 8/2017 | Wasmuth et al. | |

FOREIGN PATENT DOCUMENTS

| | | |
|---|---|---|
| CN | 101143868 A | 3/2008 |
| CN | 102512407 A | 6/2012 |
| EP | 0397350 | 11/1990 |
| EP | 0401981 | 12/1990 |
| FR | 2647676 | 12/1990 |
| JP | S62-114988 A | 5/1987 |
| JP | H01-216975 A | 8/1989 |
| JP | H03-005479 | 1/1991 |
| JP | H03-005481 | 1/1991 |
| JP | H03-258766 A | 11/1991 |
| JP | 2003-155274 A | 5/2003 |
| JP | 5934206 B2 | 6/2016 |

(Continued)

OTHER PUBLICATIONS

Alexander et al., "(Acyloxy)alkyl carbamates as novel bioreversible prodrugs for amines: increased permeation through biological membranes," J. Med. Chem., 31, pp. 318-322 (1988).

Ayres et al., "Synthesis of derivatives of cyclobuteno[c]thiophen and attempts to synthesise thiophen analogues of biphenylene," Tetrahedron, 31, pp. 1755-1760 (1975).

Berge et al., "Pharmaceutical Salts," J. Pharm. Sci., 66(1), pp. 1-19 (1977).

Beyer-Mears et al., "Glomerular Polyol Accumulation in Diabetes and its Prevention by Oral Sorbinil," Diabetes, 33(6), pp. 604-607 (Jun. 1984).

Caliceti et al., "Berberine: New Insights from Pharmacological Aspects to Clinical Evidences in the Management of Metabolic Disorders," Abstract Only, Curr. Med. Chem. 23(14), pp. 1460-1476 (2016).

(Continued)

*Primary Examiner* — Matthew P Coughlin
(74) *Attorney, Agent, or Firm* — Wilmer Cutler Pickering Hale and Dorr LLP

(57) ABSTRACT

The present disclosure relates to novel compounds and pharmaceutical compositions thereof, and methods for promoting healthy aging of skin, the treatment of skin disorders, the treatment of cardiovascular disorders, the treatment of renal disorders, the treatment of angiogenesis disorders, such as cancer, treatment of tissue damage, such as non-cardiac tissue damage, the treatment of evolving myocardial infarction, the treatment of ischemic injury, and the treatment of various other disorders, such as complications arising from diabetes with the compounds and compositions of the invention. Other disorders can include, but are not limited to, atherosclerosis, coronary artery disease, diabetic nephropathy, diabetic neuropathy, diabetic retinopathy, diabetic cardiomyopathy, infections of the skin, peripheral vascular disease, stroke, asthma, and the like.

20 Claims, No Drawings

(56) References Cited

FOREIGN PATENT DOCUMENTS

| WO | WO-91/09019 | 6/1991 | | |
|---|---|---|---|---|
| WO | WO-03/061660 | 7/2003 | | |
| WO | WO-2008/002678 | 1/2008 | | |
| WO | WO-2012/009553 | 1/2012 | | |
| WO | WO-2012009553 A1 * | 1/2012 | ........... | C07D 487/04 |

OTHER PUBLICATIONS

Cannon, "Analog Design," Burger's Medicinal Chemistry and Drug Discovery: Fifth Edition, vol. 1: Principles and Practice, Chapter Nineteen, Wiley-Interscience, pp. 783-802, 22 total pages (1995).

Chatzopoulou et al., "Novel aldose reductase inhibitors: a patent survey (2006-present)," Expert Opin. Ther. Pat., 22, pp. 1303-1323 (2012).

Cheng and González, "The effect of high glucose and oxidative stress on lens metabolism, aldose reductase, and senile cataractogenesis," Abstract Only, Metabolism, 35(4), Suppl. 1, pp. 10-14 (Apr. 1986).

Cheung et al., "Aldose Reductase Deficiency Prevents Diabetes-Induced Blood-Retinal Barrier Breakdown, Apoptosis, and Glial Reactivation in the Retina of db/db Mice," Diabetes, 54(11), pp. 3119-3125 (Nov. 2005).

ClinicalTrials.gov, "Ezetimibe Versus Nutraceuticals in Statin-intolerant Patients (ECLIPSE)," ClinicalTrials.Gov Identifier No. NCT01490229, first received Dec. 8, 2011 (4 pages).

ClinicalTrials.gov, "Low-dose Statins and Nutraceuticals in High-intensity Statin-intolerant Patients (ADHERENCE)," ClinicalTrials. Gov Identifier No. NCT02001883, first received Nov. 24, 2013 (4 pages).

Digiacomao, "Synthesis and functional evaluation of novel aldose reductase inhibitors," The Open Medicinal Chemistry Journal, 11, 2 pages (Apr. 14, 2017).

Wilson et al., "Refined 1.8 Å structure of human aldose reductase complexed with the potent inhibitor zopolrestat," Proc. Natl. Acad. Sci. USA, 90(21), pp. 9847-9851 (Nov. 1993).

Gu et al., "Effects of lignans extracted from Eucommia ulmoides and aldose reductase inhibitor epalrestat on hypertensive vascular remodeling," Abstract Only, J. Ethnopharmacol., 133(1), pp. 6-13 (Jan. 7, 2011).

Hotta et al., "Long-Term Clinical Effects of Epalrestat, an Aldose Reductase Inhibitor, on Diabetic Peripheral Neuropathy," Diabetes Care, 29(7), pp. 1538-1544 (Jul. 2006).

Hotta et al., "Stratified analyses for selecting appropriate target patients with diabetic peripheral neuropathy for long-term treatment with an aldose reductase inhibitor, epalrestat," Diabet. Med., 25(7), pp. 818-825 (2008).

Hu et al., "Efficacy and safety of aldose reductase inhibitor for the treatment of diabetic cardiovascular autonomic neuropathy: systematic review and meta-analysis," PLoS One, 9(2), e87096, pp. 1-11 (2014).

Hwang et al., "Central role for aldose reductase pathway in myocardial ischemic injury," The FASEB Journal, 18(11), pp. 1192-1199 (Aug. 2004).

International Search Report and Written Opinion for PCT Application No. PCT/US17/38505 dated Oct. 13, 2017 (21 pages).

Yagihashi et al., "Neuropathy in diabetic mice overexpressing human aldose reductase and effects of aldose reductase inhibitor," Abstract Only, Brain, 124, Pt. 12, pp. 2448-2458 (Dec. 2001).

Zeng et al., "Efficacy and safety of berberine for congestive heart failure secondary to ischemic or idiopathic dilated cardiomyopathy," Abstract Only, Am. J. Cardiol., 92(2), pp. 173-176 (Jul. 15, 2003).

Jacoby and Nesto, "Acute Myocardial Infarction in the Diabetic Patient: Pathophysiology, Clinical course and Prognosis," J. Am. Coll. Cardiol., 20(3), pp. 736-744 (1992).

Johnson et al., "Cardiac Abnormalities in Diabetic Patients With Neuropathy", Diabetes Care, 27(2), pp. 448-454 (Feb. 2004).

Kajiwara et al., "Lower incidence of myocardial infarction in type 2 diabetic patients with polyneuropathy who were treated with an aldose reductase inhibitor (epalrestat): a retrospective study," Presentation Abstract, Presentation No. 1241, 47th EASD Annual Meeting, Lisbon, 2 pages (2011).

Kalofoutis et al., "Type II diabetes mellitus and cardiovascular risk factors: Current therapeutic approaches," Exp. Clin. Cardiol., 12(1), pp. 17-28 (2007).

Kasajima et al., "Enhanced in situ expression of aldose reductase in peripheral nerve and renal glomeruli in diabetic patients," Abstract Only, Virchows Arch., 439(1), pp. 46-54 (Jul. 2001).

Kinoshita, "A thirty year journey in the polyol pathway," Exp. Eye. Res., 50(6), pp. 567-573 (1990).

Li et al., "Polyol pathway and modulation of ischemia-reperfusion injury in Type 2 diabetic BBZ rat hearts," Cardiovascular Diabetology, 7(33), 11 pages (Oct. 28, 2008).

Lightman, "Does Aldose Reductase have a role in the development of the ocular complications of diabetes?" Eye, 7, pp. 238-241 (1993).

Liu et al., "Genetic deficiency of aldose reductase counteracts the development of diabetic nephropathy in C57BL/6 mice," Diabetologia, 54(5), pp. 1242-1251 (Jan. 27, 2011).

Marin-Neto et al., "Cardiovascular effects of berberine in patients with severe congestive heart failure," Abstract Only, Clin. Cardiol., 11(4), pp. 253-260 (Apr. 1988).

Veves, "Aldose Reductase Inhibitors for the Treatment of Diabetic Neuropathy," Contemporary Diabetes: Diabetic Neuropathy: Clinical Management, Second Edition, Humana Press, chapter 18, pp. 309-320 (2007).

Mylari et al., "Novel, Potent Aldose Reductase Inhibitors: 3,4-Dihydro-4-oxo-3-[[5-(trifluoromethyl)-2-benzothiazolyl]methyl]-1-phthalazine-acetic Acid (Zopolrestat) and Congeners," J. Med. Chem., 34, pp. 108-122 (1991).

Mylari et al., "Orally Active Aldose Reductase Inhibitors: Indazoleacetic, Oxopyridazineacetic, and Oxopyridopyridazineacetic Acid Derivatives," J. Med. Chem., 35, pp. 2155-2162 (1992).

Vedantham et al., "Human Aldose Reductase Expression Accelerates Atherosclerosis in Diabetic apoE-/- Mice," Author Manuscript, published in final edited form as: Arterioscler. Thromb. Vasc. Biol. 31(8), pp. 1805-1813, (Aug. 1, 2012).

Mylari et al., "Potent, Orally Active Aldose Reductase Inhibitors Related to Zopolrestat: Surrogates for Benzothiazole Side Chain," J. Med. Chem., 35, pp. 457-465 (1992).

Nour et al., "Ischemia-Reperfusion Injury in Stroke," Intervent. Neurol., 1, pp. 185-199 (2012).

Zhou et al., "Neuroprotective effects of berberine on stroke models in vitro and in vivo," Abstract Only, Neurosci. Lett., 447(1), pp. 31-36 (Dec. 5, 2008).

Zhu, "Aldose Reductase Inhibitors as Potential Therapeutic Drugs of Diabetic Complications," Diabetes Mellitus—Insights and Perspectives, Chapter 2, pp. 17-46 (Jan. 23, 2013).

Price et al., "Mitogen-Activated Protein Kinase p38 Mediates Reduced Nerve Conduction Velocity in Experimental Diabetic Neuropathy," Diabetes, 53(7), pp. 1851-1856 (Jul. 2004).

Pubchem, Substance Record for SID 227698804, Available Date: Feb. 12, 2015, Retrieved from the Internet: <https://pubchem.ncbi.nlm.nih.gov/substance/227698804> (7 pages).

Ramana et al., "Inhibition of aldose reductase prevents growth factor-induced $G_1$-S phase transition through the AKT/phosphoinositide 3-kinase/E2F-1 pathway in human colon cancer cells," Mol. Cancer Ther., 9(4), pp. 813-824 (2010).

Ramasamy and Goldberg, "Aldose reductase and cardiovascular diseases, creating human-like diabetic complications in an experimental model," Circ. Res., 106(9), pp. 1449-1458 (May 2010).

Ramasamy et al., "Aldose reductase inhibition protects diabetic and nondiabetic rat hearts from ischemic injury," Abstract Only, Diabetes, 46(2), pp. 292-300 (Feb. 1997).

Roy et al., "The effect of an aldose reductase inhibitor on cardiovascular performance in patients with diabetes mellitus," Diabetes Research and Clinical Practice, 10(1), pp. 91-97 (1990).

Tawata et al., "Anti-platelet action of isoliquiritigenin, an aldose reductase inhibitor in licorice," Abstract Only, Eur. J. Pharmacol., 212(1), pp. 87-92 (Feb. 25, 1992).

Satoh et al., "Effect of Ranirestat on Sensory and Motor Nerve Function in Japanese Patients with Diabetic Polyneuropathy: A

(56) References Cited

OTHER PUBLICATIONS

Randomized Double-Blind Placebo-Controlled Study," J. Diabetes Res., 2016, article ID 5383797, (2016) (8 pages).

Schulz et al., "Identification of novel downstream targets of platelet glycoprotein VI activation by differential proteome analysis: implications for thrombus formation," Blood, 115(20), pp. 4102-4110 (May 20, 2010).

Sheridan, "The Most Common Replacements in Drug-Like Compounds," J. Chem. Inf. Comput. Sci., 42, pp. 103-108 (2002).

Srivastava et al., "Aldose reductase inhibition suppresses oxidative stress-induced inflammatory disorders," Author Manuscript published in final edited form as: Chem. Biol. Interact., 191, pp. 330-338 (2011).

Tammali et al., "Inhibition of aldose reductase prevents angiogenesis in vitro and in vivo," Author Manuscript, published in final edited form as: Angiogenesis, 14(2), pp. 209-221 (2011).

Tammali et al., "Inhibition of Aldose Reductase Prevents Colon Cancer Metastasis," Carcinogenesis, 32(8), pp. 1259-1267 (2011).

Tang et al., "Aldose reductase, oxidative stress, and diabetic mellitus," Frontiers in Pharmacology, 3, Article 87, 8 pages (May 9, 2012).

Tang et al., "Glucose and collagen regulate human platelet activity through aldose reductase induction of thromboxane," The Journal of Clinical Investigation, 121(11), pp. 4462-4476 (Nov. 2011).

\* cited by examiner

ALDOSE REDUCTASE INHIBITORS AND METHODS OF USE THEREOF

This application is a continuation of International Application PCT/US2017/038505, filed Jun. 21, 2017, which claims the benefit of U.S. Provisional Application No. 62/352,784, filed Jun. 21, 2016, the entire contents of which are hereby incorporated by reference in its entirety.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

The present invention relates to novel compounds and pharmaceutical compositions thereof, and methods for promoting healthy aging of skin, the treatment of skin disorders, the treatment of cardiovascular disorders, the treatment of renal disorders, the treatment of angiogenesis disorders, such as cancer, treatment of tissue damage, such as non-cardiac tissue damage, the treatment of evolving myocardial infarction, the treatment of ischemic injury, and the treatment of various other disorders, such as complications arising from diabetes with the compounds and compositions of the invention. Other disorders can include, but are not limited to, atherosclerosis, coronary artery disease, diabetic nephropathy, diabetic neuropathy, diabetic retinopathy, diabetic cardiomyopathy, infections of the skin, peripheral vascular disease, stroke, asthma, and the like.

BACKGROUND OF THE INVENTION

Diabetes is one of the most common chronic disorders, in which high blood glucose levels result from a lack of insulin production and/or insulin sensitivity. Individuals with high blood glucose metabolize more glucose via a glucose to sorbitol to fructose pathway in insulin insensitive cells such as lenses, peripheral nerves and glomerulus. This leads to an overabundance of sorbitol in the cells, which is not easily diffused through the cell membrane. The increased concentration of sorbitol triggers an influx of water into the cells, causing swelling and potential damage.

Aldose reductase (AR) is a monomeric, NADPH-dependent oxidoreductase from the aldo-keto reductase family of enzymes. It is an enzyme that is present in many parts of the body. Aldose reductase catalyzes the reduction of saturated and unsaturated aldehydes, including aldo sugars and monosaccharides, as well as a broad array of other substrates. Primarily, aldose reductase catalyzes the reduction of glucose to sorbitol, one of the steps in the sorbitol pathway that is responsible for fructose formation from glucose. Aldose reductase activity increases as the glucose concentration rises in diabetic conditions where tissues are no longer insulin sensitive. These tissues include, for example, lenses, peripheral nerves and glomerulus of the kidney. Sorbitol cannot easily diffuse through cell membranes and therefore accumulates, causing osmotic damage, which in turn leads to retinopathy, neuropathy, nephropathy, and cardiomyopathy. The mechanism of damage also occurs through increased oxidative stress and damage, and an increased amount of advanced glycation endproducts. Therefore, inhibition of aldose reductase could prevent the buildup of sorbitol in insulin insensitive cells in diabetics, and presents a novel method to prevent the macrovascular and microvascular complications in diabetic patients. In addition, aldose reductase inhibitors, such as zopolrestat, may aid in treating or ameliorating such effects and have shown efficacy in wound healing in the corneal epithelium of diabetic animal models. Lastly, AR has recently been implicated in a wide range of therapeutic areas including cancer, myocardial infarction and ischemic injury, asthma, and transplantation.

Previous clinical trials have shown that while aldose reductase inhibitors are well tolerated by patients, they are minimally effective in combating disease. These failures have been attributed to the current aldose reductase inhibitors possessing poor activity and short half-life, resulting in decreased efficacy. Additionally, some aldose reductase inhibitors are toxic. Thus, there is a need for new aldose reductase inhibitor compounds.

SUMMARY

It is understood that any of the embodiments described below can be combined in any desired way, and that any embodiment or combination of embodiments can be applied to each of the aspects described below, unless the context indicates otherwise.

In one aspect, the invention provides a compound of Formula (I)

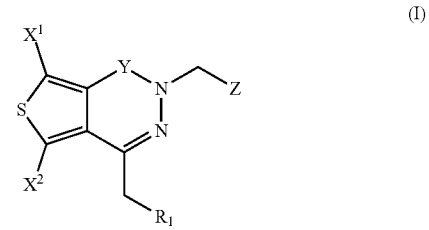

wherein,
$R^1$ is $CO_2R^2$ or $CO_2^-X^+$;
$R^2$ is H, $(C_1-C_6)$-alkyl, $(C_1-C_6)$-hydroxyalkyl, or $(C_1-C_6)$-aminoalkyl;
$X^1$ is H or halogen;
$X^2$ is H or halogen;
Y is a bond, C=O, C=S, C=NH, or C=N$(C_1-C_4)$-alkyl;
Z is

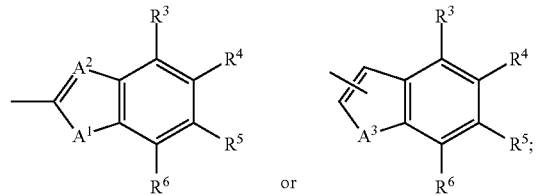

$A^1$ is $NR^7$, O, S or $CH_2$;
$A^2$ is N or CH;
$A^3$ is $NR^7$, O, or S;

$R^3$ through $R^6$ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl;

$R^7$ is hydrogen, $C_1-C_4$ alkyl, or $C(O)O-(C_1-C_4)$-alkyl; and $X^+$ is a counter ion; or a pharmaceutically acceptable salt or solvate thereof.

In some embodiments, $R^2$ is hydrogen or $(C_1-C_6)$-alkyl;
Y is C=O;
$A^1$ is $NR^7$, O, or S;
$A^2$ is N;
$A^3$ is O, or S; and
$R^3$ through $R^6$ are independently hydrogen, halogen, cyano, acyl, haloalkyl, haloalkoxy, haloalkylthio, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl;
or a pharmaceutically acceptable salt or solvate thereof.

In some embodiments, $R^2$ is hydrogen or tert-butyl;
$R^3$ through $R^6$ are independently hydrogen, halogen, or haloalkyl; and
$R^7$ is hydrogen, $(C_1-C_4)$-alkyl, or C(O)O-tert-butyl; or a pharmaceutically acceptable salt or solvate thereof.

In some embodiments, Z is

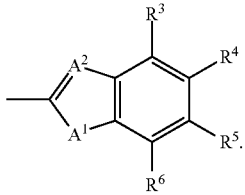

In some embodiments, $R^2$ is hydrogen or $(C_1-C_6)$-alkyl;
Y is C=O;
$A^1$ is $NR^7$, O, or S;
$A^2$ is N;
$R^3$ through $R^6$ are independently hydrogen, halogen, cyano, acyl, haloalkyl, haloalkoxy, haloalkylthio, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl; and
$R^7$ is hydrogen, $C_1-C_4$ alkyl, or $C(O)O-(C_1-C_4)$-alkyl; or a pharmaceutically acceptable salt or solvate thereof.

In some embodiments, $R^2$ is hydrogen or tert-butyl;
Y is C=O;
$A^1$ is $NR^7$, O or S;
$A^2$ is N;
$R^3$ through $R^6$ are independently hydrogen, halogen, or haloalkyl; and
$R^7$ is hydrogen, $(C_1-C_4)$-alkyl, or C(O)O-tert-butyl; or a pharmaceutically acceptable salt or solvate thereof.

In some embodiments, $R^2$ is hydrogen or tert-butyl;
Y is C=O;
$A^1$ is $NR^7$, O or S;
$A^2$ is N;
$R^3$ through $R^6$ are independently hydrogen, halogen, or $CF_3$; and
$R^7$ is hydrogen, $(C_1-C_4)$-alkyl, or C(O)O-tert-butyl; or a pharmaceutically acceptable salt or solvate thereof.

In some embodiments, $R^2$ is hydrogen;
$X^1$ is H;
$X^2$ is H;
Y is C=O;
$A^1$ is S;
$A^2$ is N;

$R^3$ through $R^6$ are independently hydrogen, halogen, or haloalkyl; and
$R^7$ is hydrogen, $(C_1-C_4)$-alkyl, or C(O)O-tert-butyl; or a pharmaceutically acceptable salt or solvate thereof.

In some embodiments, $R^2$ is hydrogen;
$X^1$ is H;
$X^2$ is H;
Y is C=O;
$A^1$ is S;
$A^2$ is N;
$R^3$, $R^5$, and $R^6$ are hydrogen;
$R^4$ is hydrogen, halogen, or haloalkyl; and
$R^7$ is hydrogen, $(C_1-C_4)$-alkyl, or C(O)O-tert-butyl; or a pharmaceutically acceptable salt or solvate thereof.

In some embodiments, the compound of Formula (I) is represented by the formula

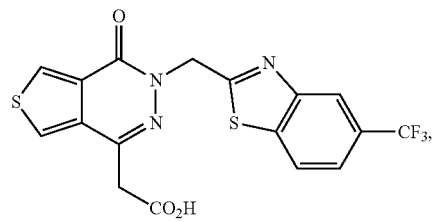

or a pharmaceutically acceptable salt or solvate thereof.

In some embodiments, $R^2$ is hydrogen;
$X^1$ is Cl;
$X^2$ is Cl;
Y is C=O;
$A^1$ is S;
$A^2$ is N;
$R^3$ through $R^6$ are independently hydrogen, halogen, or haloalkyl; and
$R^7$ is hydrogen, $(C_1-C_4)$-alkyl, or C(O)O-tert-butyl; or a pharmaceutically acceptable salt or solvate thereof.

In some embodiments, $R^2$ is hydrogen;
$X^1$ is Cl;
$X^2$ is Cl;
Y is C=O;
$A^1$ is S;
$A^2$ is N;
$R^3$, $R^5$, and $R^6$ are hydrogen;
$R^4$ is hydrogen, halogen, or haloalkyl; and
$R^7$ is hydrogen, $(C_1-C_4)$-alkyl, or C(O)O-tert-butyl; or a pharmaceutically acceptable salt or solvate thereof.

In some embodiments, the compound of Formula (I) is represented by the formula

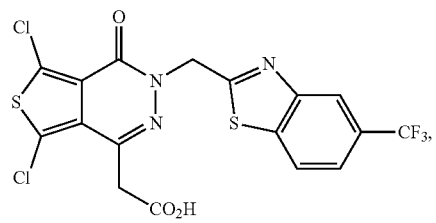

or a pharmaceutically acceptable salt or solvate thereof.

In some embodiments, Z is

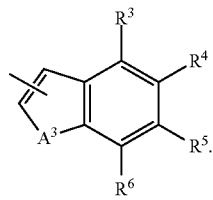

In some embodiments, $R^2$ is hydrogen or $(C_1-C_6)$-alkyl;
Y is C=O;
$R^3$ through $R^6$ are independently hydrogen, halogen, cyano, acyl, haloalkyl, haloalkoxy, haloalkylthio, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl; and
$R^7$ is hydrogen, $C_1-C_4$ alkyl, or $C(O)O-(C_1-C_4)$-alkyl; or a pharmaceutically acceptable salt or solvate thereof.

In some embodiments, $R^2$ is hydrogen or tert-butyl;
Y is C=O;
$R^3$ through $R^6$ are independently hydrogen, halogen, or haloalkyl; and
$R^7$ is hydrogen, $(C_1-C_4)$-alkyl, or C(O)O-tert-butyl; or a pharmaceutically acceptable salt or solvate thereof.

In some embodiments, $R^2$ is hydrogen or tert-butyl;
Y is C=O;
$R^3$ through $R^6$ are independently hydrogen or halogen; and
$R^7$ is hydrogen, $(C_1-C_4)$-alkyl, or C(O)O-tert-butyl; or a pharmaceutically acceptable salt or solvate thereof.

In some embodiments, $R^2$ is hydrogen;
$X^1$ is H;
$X^2$ is H;
Y is C=O;
$R^3$ through $R^6$ are independently hydrogen, halogen, or haloalkyl; and
$R^7$ is hydrogen, $(C_1-C_4)$-alkyl, or C(O)O-tert-butyl; or a pharmaceutically acceptable salt or solvate thereof.

In some embodiments, $R^2$ is hydrogen;
$X^1$ is H;
$X^2$ is H;
Y is C=O;
$R^3$, $R^5$, and $R^6$ are hydrogen;
$R^4$ is hydrogen or halogen; and
$R^7$ is hydrogen, $(C_1-C_4)$-alkyl, or C(O)O-tert-butyl; or a pharmaceutically acceptable salt or solvate thereof.

In some embodiments, the compound of Formula (I) is represented by the formula

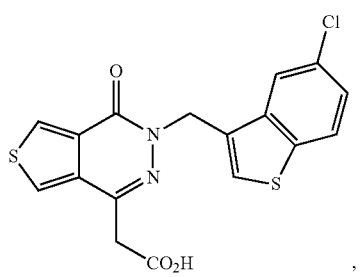

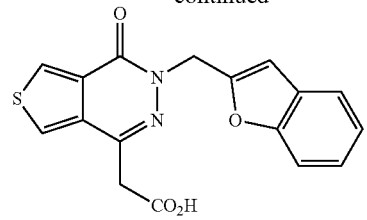

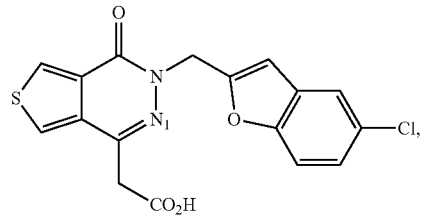

or a pharmaceutically acceptable salt or solvate thereof.

In some embodiments, $R^2$ is hydrogen;
$X^1$ is Cl;
$X^2$ is Cl;
Y is C=O;
$R^3$ through $R^6$ are independently hydrogen, halogen, or haloalkyl; and
$R^7$ is hydrogen, $(C_1-C_4)$-alkyl, or C(O)O-tert-butyl; or a pharmaceutically acceptable salt or solvate thereof.

In some embodiments, $R^2$ is hydrogen;
$X^1$ is Cl;
$X^2$ is Cl;
Y is C=O;
$A^3$ is is $NR^7$, O or S; and
$R^3$, $R^5$, and $R^6$ are hydrogen;
$R^4$ is hydrogen or halogen; and
$R^7$ is hydrogen, $(C_1-C_4)$-alkyl, or C(O)O-tert-butyl; or a pharmaceutically acceptable salt or solvate thereof.

In some embodiments, the compound of Formula (I) is selected from the group consisting of:

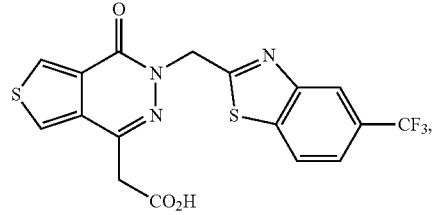 [SMILES: O=C(O)Cc1nn(Cc2nc3cc(C(F)(F)F)ccc3s2)c(=O)c2cscc12]

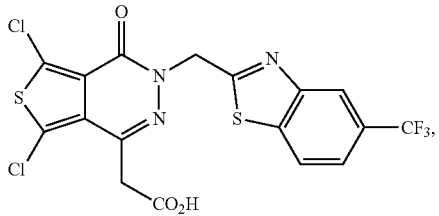

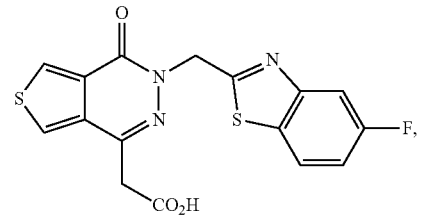

[Structures of thienopyridazinone acetic acid derivatives with various heterocyclic substituents: benzothiazole, 5-chlorobenzothiophene, 6-chlorobenzothiazole, 6-fluorobenzoxazole, benzofuran, and 5-chlorobenzofuran]

In some embodiments, the counter ion is selected from the group consisting of: sodium, lithium, potassium, calcium, magnesium, zinc, ammonium, and tetrafluoroborate.

In some embodiments, the counter ion is selected from the group consisting of:

[Structures of counter ions: arginine, lysine, aspartate, glutamate, glucosamine, meglumine, and 1,1,3,3-tetramethylguanidine derivative]

In another aspect, the invention provides a pharmaceutical composition comprising a compound of Formula (I) and a pharmaceutically acceptable carrier.

In another aspect, the invention provides a method of inhibiting aldose reductase activity in a subject comprising administration of a therapeutically effective amount of a compound of Formula (I) to a subject in need thereof.

In some embodiments, the subject is diabetic.

In some embodiments, the subject is a human.

In another aspect, the invention provides a method of treating a disorder in a subject comprising administration of a therapeutically effective amount of a compound of Formula (I) to a subject in need thereof.

In some embodiments, the disorder is atherosclerosis.

In some embodiments, the disorder is diabetic nephropathy.

In some embodiments, the disorder is diabetic neuropathy.

In some embodiments, the disorder is diabetic retinopathy.

In some embodiments, the disorder is a cardiovascular disease.

In some embodiments, the disorder is peripheral vascular disease.

In some embodiments, the disorder is an angiogenesis disorder.

In some embodiments, the disorder is tissue damage.

In some embodiments, the disorder is diabetic cardiomyopathy.

In another aspect, the invention provides a method to treat a skin disorder or promote healthy aging of skin, comprising applying to a dermal substrate a therapeutically effective amount of a compound of Formula (I), or a pharmaceutical composition comprising a compound of Formula (I) and a pharmaceutically acceptable carrier, to a subject in need thereof.

In some embodiments, the dermal substrate is human skin.

In another aspect, the invention provides a method of treating a subject with evolving myocardial infarction comprising: administering a therapeutically effective amount of a compound of Formula (I), or a pharmaceutical composition comprising a compound of Formula (I) and a pharmaceutically acceptable carrier, to a subject in need thereof.

The present invention is based, in part, on certain discoveries which are described more fully in the Examples section of the present application. For example, the present invention is based, in part, on the discovery of compounds of formula (I) and the aldose reductase inhibition exhibited by such compounds.

These and other embodiments of the invention are further described in the following sections of the application, including the Detailed Description, Examples, and Claims. Still other objects and advantages of the invention will become apparent by those of skill in the art from the disclosure herein, which are simply illustrative and not restrictive. Thus, other embodiments will be recognized by the ordinarily skilled artisan without departing from the spirit and scope of the invention.

DETAILED DESCRIPTION

Aldose reductase inhibitors are described, for example, in U.S. Pat. Nos. 8,916,563; 5,677,342; 5,304,557; 5,155,259; 4,954,629; 4,939,140; U.S. Publication Number US 2006/0293265; Roy et al., in *Diabetes Research and Clinical Practice* 1990, 10(1), 91-97; CN101143868A; and Chatzopoulou et al., in *Expert Opin. Ther. Pat.* 2012, 22, 1303; and references cited therein; each of which hereby incorporated by reference in its entirety. Aldose reductase inhibitors include, for example, zopolrestat, epalrestat, ranirestat, berberine and sorbinil. A novel family of aldose reductase inhibitors has been discovered and is described herein. Surprisingly, this novel family comprises compounds that exhibit dramatically improved properties such as, for example, binding affinity, solubility, and polarity relative to other aldose reductase inhibitors such as, for example, zopolrestat. Compounds such as zopolrestat are described, for example in U.S. Pat. Nos. 4,939,140; 6,159,976; and 6,570,013; each of which hereby incorporated by reference in its entirety.

The compounds and/or compositions of the invention may be effective in treating, reducing, and/or suppressing complications related to aldose reductase activity such as, for example, atherosclerosis, neuropathy, retinopathy, nephropathy, cardiomyopathy, and multiple complications in diabetic patients. The compounds and/or compositions of the invention may also be effective in treating, reducing, and/or reducing cardiovascular and renal disorders in non-diabetic patients, as well as promoting healthy aging of skin or wound healing. Treatment using aldose reductase inhibitors is described in, e.g., CN102512407A; WO2008002678A2; CN101143868A; Srivastava et al., in *Chem Biol Interact.* 2011, 30, 330; Hu et al., in *PLoS One* 2014, 9(2), e87096; Satoh et al., in *J Diabetes Res.* 2016, 2016, 5383797; Chatzopoulou et al., in *Expert Opin. Ther. Pat.* 2012, 22, 1303; each of which is hereby incorporated by reference in its entirety.

Abbreviations and Definitions

The term "aldose reductase inhibitor" refers to compounds and salts or solvates thereof that function by inhibiting the activity of the enzyme aldose reductase, which is primarily responsible for regulating metabolic reduction of aldoses. Exemplary aldoses include, but are not limited to, glucose or galactose, and their corresponding polyols, such as sorbitols and galactitols. Exemplary aldose reductase inhibitors may be found in U.S. Pat. Nos. 8,916,563; 5,677,342; 5,304,557; 5,155,259; 4,954,629; 4,939,140; U.S. Publication Number US 2006/0293265; and Roy et al., in *Diabetes Research and Clinical Practice* 1990, 10(1), 91-97; and each of which hereby incorporated by reference in its entirety.

The term "compound of the invention" as used herein means a compound of formula (I). The term is also intended to encompass salts, hydrates, pro-drugs and solvates thereof.

The term "composition(s) of the invention" as used herein means compositions comprising a compound of the invention, and salts, hydrates, pro-drugs, or solvates thereof. The compositions of the invention may further comprise other agents such as, for example, excipients, stabilants, lubricants, solvents, and the like.

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, where the one or more substituents are independently $C_1$-$C_{10}$ alkyl. Examples of "alkyl" groups include methyl, ethyl, propyl, isopropyl, butyl, isobutyl, sec-butyl, tert-butyl, pentyl, hexyl, heptyl, cyclopropyl, cyclobutyl, cyclopentyl, cyclohexyl, cycloheptyl, norbornyl, and the like.

The term "solvate" as used herein means a compound, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, for example sodium, potassium, calcium, magnesium, zinc, ammonia, lysine, arginine, histidine, polyhydroxylated amines or tetrafluoroborate. Exemplary pharmaceutically acceptable salts are found, for example, in Berge, et al. (*J. Pharm. Sci.* 1977, 66(1), 1; and U.S. Pat. Nos. 6,570,013 and 4,939,140; (each hereby incorporated by reference in its entirety). Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glyco-heptonic acid and lactobionic acid.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of afflictions related to aldose reductase, or one or more symptoms thereof, prevent the advancement of conditions or symptoms related to afflictions related to aldose reductase, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment.

The phrase "in need thereof" refers to the need for symptomatic or asymptomatic relief from conditions related to aldose reductase activity or that may otherwise be relieved by the compounds and/or compositions of the invention.

In one embodiment, aldose reductase inhibitors described herein encompass compounds of Formula (I) or pharmaceutically acceptable salts, pro-drugs and solvates thereof,

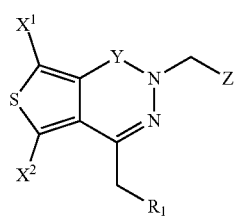

(I)

wherein,
$R^1$ is $CO_2R^2$ or $CO_2^-X^+$;
$R^2$ is H, $(C_1-C_6)$-alkyl, $(C_1-C_6)$-hydroxyalkyl, or $(C_1-C_6)$-aminoalkyl;
$X^1$ is H or halogen;
$X^2$ is H or halogen;
Y is a bond, C=O, C=S, C=NH, or C=N($C_1-C_4$)-alkyl;
Z is

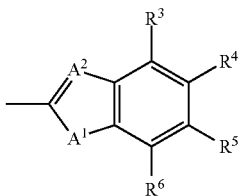 or 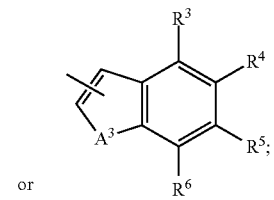

$A^1$ is $NR^7$, O, S or $CH_2$;
$A^2$ is N or CH;
$A^3$ is $NR^7$, O, or S;
$R^3$ through $R^6$ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl;
$R^7$ is hydrogen, $C_1-C_4$ alkyl, or $C(O)O—(C_1-C_4)$-alkyl; and
$X^+$ is a counter ion.

It will be recognized by those of skill in the art that the designation of
Z is

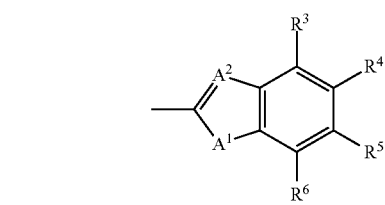

or Z is

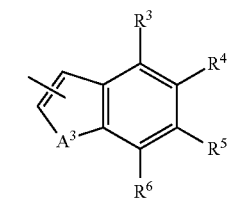

indicates that when Z is

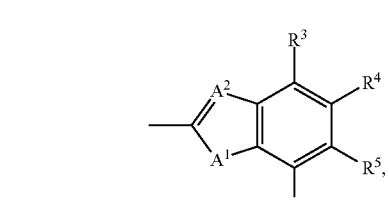

the compounds of Formula (I) are understood to encompass

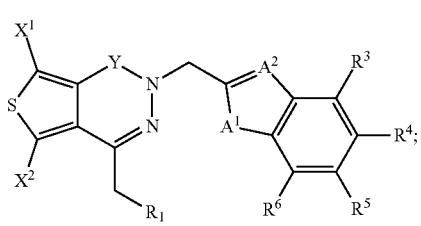

and when Z is

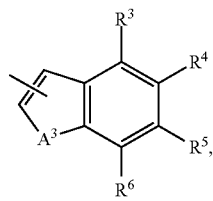

the compounds of Formula (I) are understood to encompass

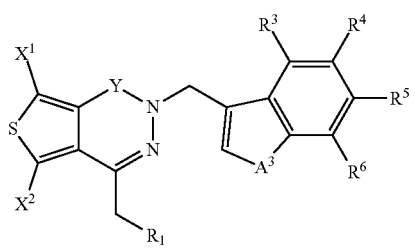

and

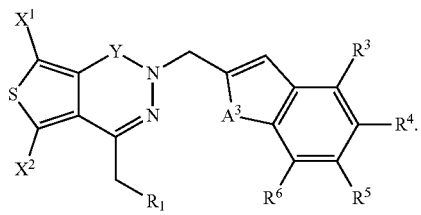

In certain embodiments, $R^1$ is $CO_2R^2$ or $CO_2^-X^+$. In certain embodiments, $R^1$ is $CO_2R^2$. In certain embodiments, $R^1$ is $CO_2^-X^+$.

In certain embodiments, $R^2$ is hydrogen or $(C_1-C_6)$-alkyl. In certain embodiments, $R^2$ is hydrogen or $(C_1-C_4)$-alkyl. In certain embodiments, $R^2$ is hydrogen or $(C_1-C_3)$-alkyl. In certain embodiments, $R^2$ is hydrogen, methyl, or ethyl. In certain embodiments, $R^2$ is hydrogen or methyl. In certain embodiments, $R^2$ is methyl or ethyl. In certain embodiments, $R^2$ is methyl. In certain embodiments, $R^2$ is hydrogen. In certain embodiments, $R^2$ is $(C_1-C_6)$-alkyl. In certain embodiments, $R^2$ is $(C_1-C_6)$-n-alkyl. In certain embodiments, $R^2$ is $(C_1-C_2)$-alkyl. In certain embodiments, $R^2$ is $(C_1-C_3)$-alkyl. In certain embodiments, $R^2$ is $(C_1-C_4)$-alkyl. In certain embodiments, $R^2$ is tert-butyl.

In certain embodiments, $R^3$ through $R^6$ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl.

In certain embodiments, $R^3$ through $R^6$ are independently hydrogen, halogen or haloalkyl. In certain embodiments, $R^3$ through $R^6$ are independently hydrogen, halogen or trihaloalkyl.

In certain embodiments, $R^3$ and $R^6$ are hydrogen. In certain embodiments, $R^3$, $R^5$, and $R^6$ are hydrogen.

In certain embodiments, $R^4$ is hydrogen, halogen or haloalkyl. In certain embodiments, $R^4$ is hydrogen. In certain embodiments, $R^4$ is halogen. In certain embodiments, $R^4$ is haloalkyl. In certain embodiments, $R^4$ is $CF_3$.

In certain embodiments, $R^3$ through $R^6$ are hydrogen. In certain embodiments, $R^3$, $R^5$, $R^6$ are hydrogen and $R^4$ is halogen or haloalkyl. In certain embodiments, $R^3$, $R^5$, $R^6$ are hydrogen and $R^4$ is haloalkyl. In certain embodiments, $R^3$, $R^5$, $R^6$ are hydrogen and $R^4$ is $CF_3$. In certain embodiments, $R^3$, $R^5$, $R^6$ are hydrogen and $R^4$ is halogen. In certain embodiments, $R^3$, $R^5$, $R^6$ are hydrogen and $R^4$ is F. In certain embodiments, $R^3$, $R^5$, $R^6$ are hydrogen and $R^4$ is Cl.

In certain embodiments, Y is C=O, C=S, C=NH, or C=N($C_1-C_4$)-alkyl. In certain embodiments, Y is C=O or C=S. In certain embodiments, Y is C=O. In certain embodiments, Y is C=S. In certain embodiments, Y is C=NH, or C=N($C_1-C_4$)-alkyl.

In certain embodiments, $A^1$ is $NR^7$, O, S or $CH_2$. In certain embodiments, $A^1$ is $NR^7$, O, or S. In certain embodiments, $A^1$ is $NR^7$, S or $CH_2$. In certain embodiments, $A^1$ is $NR^7$ or O. In certain embodiments, $A^1$ is $NR^7$ or S. In certain embodiments, $A^1$ is $NR^7$. In certain embodiments, $A^1$ is O. In certain embodiments, $A^1$ is S.

In certain embodiments, $A^2$ is N or CH. In certain embodiments, $A^2$ is N. In certain embodiments, $A^2$ is CH.

In certain embodiments, $A^3$ is $NR^7$, O, or S. In certain embodiments, $A^3$ is O. In certain embodiments, $A^3$ is S. In certain embodiments, $A^3$ is $NR^7$.

In certain embodiments, $X^1$ and $X^2$ are hydrogen.

In certain embodiments, $X^1$ and $X^2$ are halogen. In certain embodiments, $X^1$ and $X^2$ are Cl.

In certain embodiments, $X^1$ and $X^2$ are independently hydrogen or halogen. In certain embodiments, $X^1$ is hydrogen and $X^2$ is Cl. In certain embodiments, $X^1$ is Cl and $X^2$ is hydrogen.

In certain embodiments, Z is

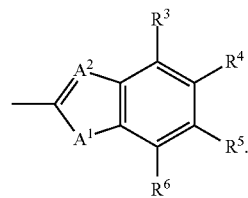

In certain embodiments, Z is

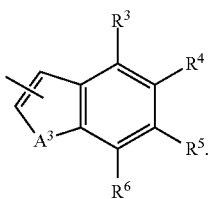

In certain embodiments, $R^7$ is hydrogen, $C_1-C_4$ alkyl, or C(O)O—$(C_1-C_4)$-alkyl. In certain embodiments, $R^7$ is hydrogen. In certain embodiments, $R^7$ is $C_1$-$C_4$ alkyl. In certain embodiments, $R^7$ is $C_1$-$C_3$ alkyl. In certain embodiments, $R^7$ is $C_1$-$C_2$ alkyl. In certain embodiments, $R^7$ is $C_1$-$C_4$ n-alkyl. In certain embodiments, $R^7$ is $C_1$-$C_3$ n-alkyl. In certain embodiments, $R^7$ is C(O)O—($C_1$-$C_4$)-alkyl. In certain embodiments, $R^7$ is C(O)O—($C_1$-$C_3$)-alkyl. In certain embodiments, $R^7$ is C(O)O—($C_1$-$C_2$)-alkyl. In certain embodiments, $R^7$ is C(O)O—($C_1$-$C_4$)-n-alkyl. In certain embodiments, $R^7$ is C(O)O—($C_1$-$C_3$)-n-alkyl.

In certain embodiments, $R^1$ is $CO_2R^2$;
$R^2$ is H or ($C_1$-$C_6$)-alkyl;
$X^1$ is H;
$X^2$ is H;
Y is C=O;
Z is

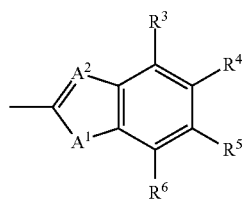 or 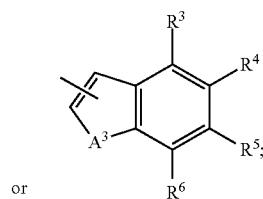

$A^1$ is $NR^7$, O, or S;
$A^2$ is N;
$A^3$ is O or S;
$R^3$ through $R^6$ are independently hydrogen, halogen, cyano, acyl, haloalkyl, haloalkoxy, haloalkylthio, trifluoroacetyl, ($C_1$-$C_4$)-alkyl, ($C_1$-$C_4$)-alkoxy, ($C_1$-$C_4$)-alkylthio, ($C_1$-$C_4$)-alkylsulfinyl, or ($C_1$-$C_4$)-alkylsulfonyl; and
$R^7$ is hydrogen, $C_1$-$C_4$ alkyl, or C(O)O—($C_1$-$C_4$)-alkyl.

In certain embodiments, $R^1$ is $CO_2R^2$;
$R^2$ is H or tert-butyl;
$X^1$ is H;
$X^2$ is H;
Y is C=O;
Z is

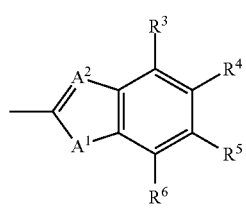 or 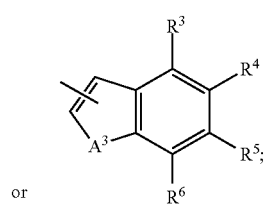

$A^1$ is $NR^7$, O, or S;
$A^2$ is N;
$A^3$ is O or S;
$R^3$ through $R^6$ are independently hydrogen, halogen, haloalkyl; and
$R^7$ is hydrogen, $C_1$-$C_4$ alkyl, or C(O)O—($C_1$-$C_4$)-alkyl.

In certain embodiments, $R^1$ is $CO_2R^2$;
$R^2$ is H or tert-butyl;
$X^1$ is H;
$X^2$ is H;
Y is C=O;

Z is

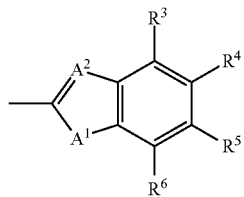 or 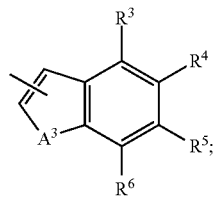

$A^1$ is $NR^7$, O, or S;
$A^2$ is N;
$A^3$ is O or S;
$R^3$, $R^5$, and $R^6$ are hydrogen;
$R^4$ is hydrogen, halogen, or haloalkyl; and
$R^7$ is hydrogen, $C_1$-$C_4$ alkyl, or C(O)O—($C_1$-$C_4$)-alkyl.

In certain embodiments, $R^1$ is $CO_2R^2$;
$R^2$ is H or ($C_1$-$C_6$)-alkyl;
$X^1$ is halogen;
$X^2$ is halogen;
Y is C=O;
Z is

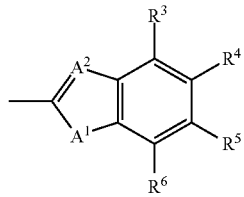 or 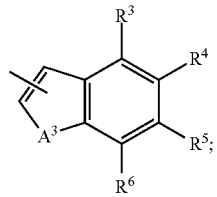

$A^1$ is $NR^7$, O, or S;
$A^2$ is N;
$A^3$ is O or S;
$R^3$ through $R^6$ are independently hydrogen, halogen, cyano, acyl, haloalkyl, haloalkoxy, haloalkylthio, trifluoroacetyl, ($C_1$-$C_4$)-alkyl, ($C_1$-$C_4$)-alkoxy, ($C_1$-$C_4$)-alkylthio, ($C_1$-$C_4$)-alkylsulfinyl, or ($C_1$-$C_4$)-alkylsulfonyl; and
$R^7$ is hydrogen, $C_1$-$C_4$ alkyl, or C(O)O—($C_1$-$C_4$)-alkyl.

In certain embodiments, $R^1$ is $CO_2R^2$;
$R^2$ is H or tert-butyl;
$X^1$ is halogen;
$X^2$ is halogen;
Y is C=O;
Z is

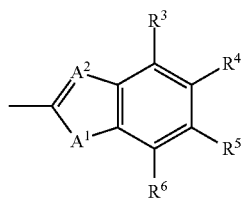 or 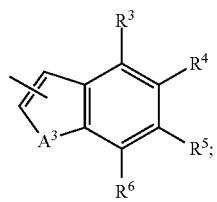

$A^1$ is $NR^7$, O, or S;
$A^2$ is N;
$A^3$ is O or S;
$R^3$ through $R^6$ are independently hydrogen, halogen, haloalkyl; and
$R^7$ is hydrogen, $C_1$-$C_4$ alkyl, or C(O)O—($C_1$-$C_4$)-alkyl.

In certain embodiments, $R^1$ is $CO_2R^2$;

$R^2$ is H or tert-butyl;
$X^1$ is Cl;
$X^2$ is Cl;
Y is C=O;
Z is

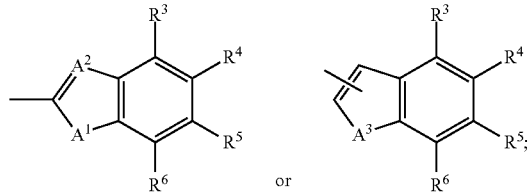

or $A^1$ is $NR^7$, O, or S;
$A^2$ is N;
$A^3$ is O or S;
$R^3$ through $R^6$ are independently hydrogen, halogen, haloalkyl; and
$R^7$ is hydrogen, $C_1$-$C_4$ alkyl, or C(O)O—($C_1$-$C_4$)-alkyl.

In certain embodiments, $R^1$ is $CO_2R^2$;
$R^2$ is H or tert-butyl;
$X^1$ is Cl;
$X^2$ is Cl;
Y is C=O;
Z is

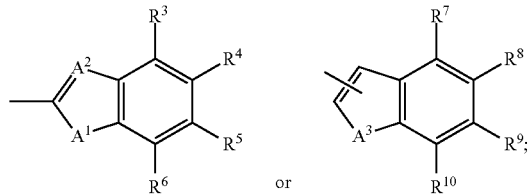

or $A^1$ is $NR^7$, O, or S;
$A^2$ is N;
$A^3$ is O or S;
$R^3$, $R^5$, and $R^6$ are hydrogen;
$R^4$ is hydrogen, halogen, or haloalkyl; and
$R^7$ is hydrogen, $C_1$-$C_4$ alkyl, or C(O)O—($C_1$-$C_4$)-alkyl.

In certain embodiments, the compound of Formula (I) is selected from the group consisting of:

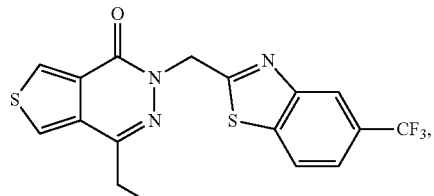

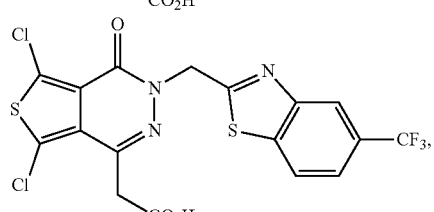

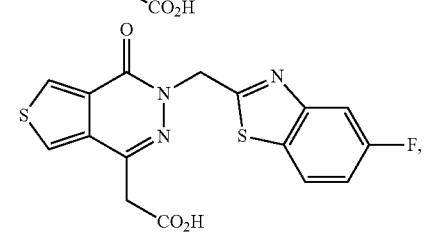

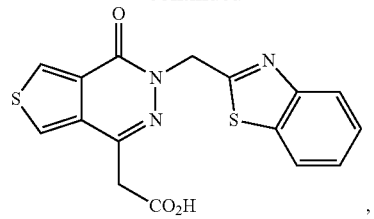

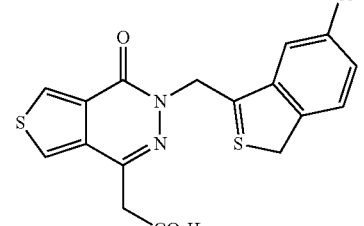

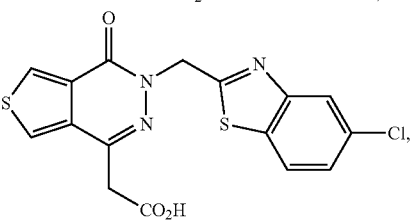

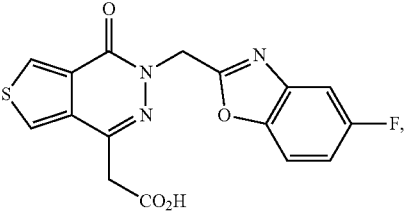

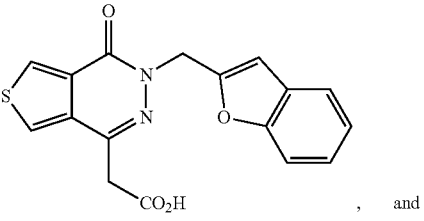

, and

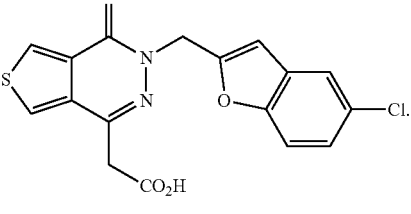

In certain embodiments, the compound of Formula (I) is

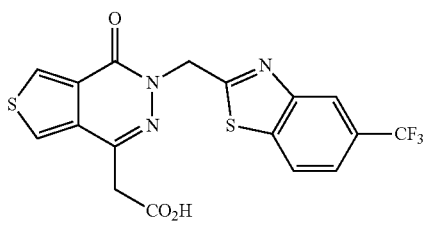 [SMILES: O=C(O)Cc1nn(Cc2nc3cc(C(F)(F)F)ccc3s2)c(=O)c2cscc12]

or a pharmaceutically acceptable salt thereof.

In certain embodiments, the compound of formula (I) is

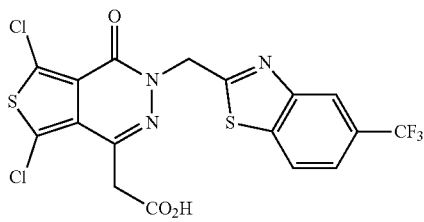 [SMILES: O=C(O)Cc1nn(Cc2nc3cc(C(F)(F)F)ccc3s2)c(=O)c2c(Cl)sc(Cl)c12]

or a pharmaceutically acceptable salt thereof.

In certain embodiments, X⁺ is a counter ion. In certain embodiments, the counter ion is sodium, lithium, potassium, calcium, ammonium, or tetrafluoroborate. In certain embodiments, the counter ion is sodium, lithium, potassium, calcium, ammonium, or a protonated amino acid. In certain embodiments, the counter ion is sodium, lithium, potassium, ammonium, or a protonated amino acid. In certain embodiments, the counter ion is sodium or ammonium. In certain embodiments, the counter ion is lithium or potassium. In certain embodiments, the counter ion is sodium, ammonium, or an amino acid. In certain embodiments, the counter ion is potassium, ammonium, or an amino acid. In certain embodiments, the counter ion is sodium or calcium. In certain embodiments, the counter ion is lithium, potassium, or calcium. In certain embodiments, the counter ion is sodium. In certain embodiments, the counter ion is lithium. In certain embodiments, the counter ion is potassium. In certain embodiments, the counter ion is calcium. In certain embodiments, the counter ion is ammonium. In certain embodiments, the counter ion is tetrafluoroborate. In some embodiments, the compound of Formula (I) is highly water soluble when X⁺ is a counter ion. It is well known in the art that highly water soluble medicinal preparations, when administered orally, result in efficient absorption of such preparations from the gastrointestinal tract into systemic circulation. Another hallmark of such preparations is the rapid rate at which they are absorbed into the systemic circulation resulting in a high concentration of the active agent in the blood. Also, water soluble preparations are especially suitable for parenteral administration, for example, intravenous administration.

In certain embodiments, the counter ion is a protonated amino acid or a protonated aminoglycoside. In certain embodiments, the aminoglycoside is glucosamine, galactosamine, mannosamine, or muramic acid. In certain embodiments, the aminoglycoside is glucosamine, galactosamine, or mannosamine. In certain embodiments, the aminoglycoside is glucosamine or galactosamine. In certain embodiments, the aminoglycoside is glucosamine. In certain embodiments, the aminoglycoside is galactosamine. In certain embodiments, the amino acid is lysine, arginine, or histidine. In certain embodiments, the amino acid is lysine or arginine. In certain embodiments, the amino acid is lysine. In certain embodiments, the amino acid is arginine.

In certain embodiments, the counter ion is

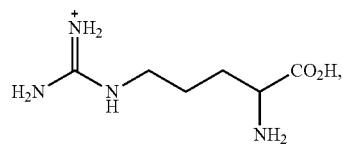

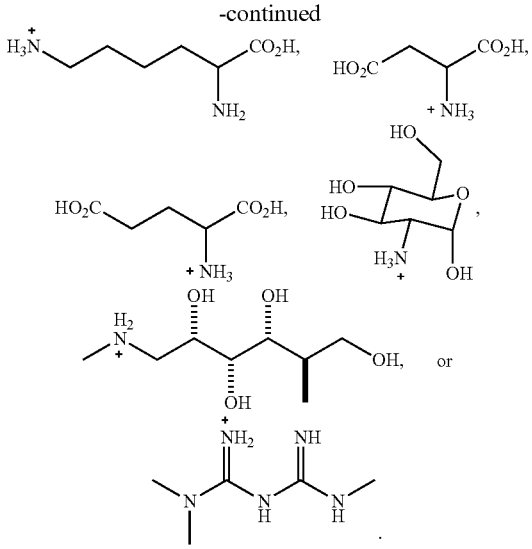

In certain embodiments, the counter ion is

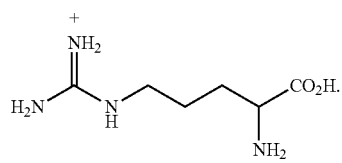 [SMILES: N=C(N)NCCCC(N)C(=O)O]

In certain embodiments, the counter ion is

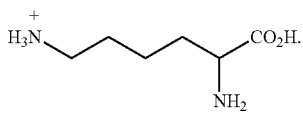

In certain embodiments, the counter ion is

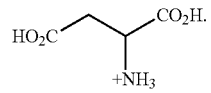

In certain embodiments, the counter ion is

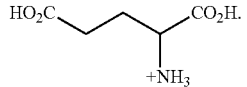

In certain embodiments, the counter ion is

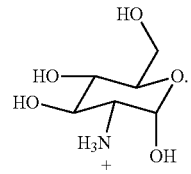 [SMILES: NC1C(O)OC(CO)C(O)C1O]

In certain embodiments, the counter ion is

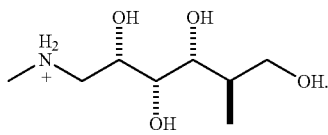

In certain embodiments, the counter ion is

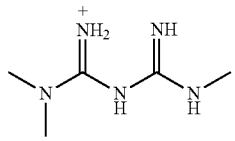

Synthesis

The compounds described herein can be prepared according to known processes. Schemes 1-4 represent general synthetic schemes for preparing compounds of formula (I). These schemes are illustrative and are not meant to limit the possible techniques one skilled in the art may use to prepare compounds disclosed herein. Different methods will be evident to those skilled in the art. Various modifications to these methods may be envisioned by those skilled in the art to achieve similar results to that of the inventors provided below. For example, optional protecting groups can be used as described, for example, in Greene et al., *Protective Groups in Organic Synthesis* (4th ed. 2006).

The compounds of Formula (I-1) can generally be prepared, for example, according to Scheme 1:

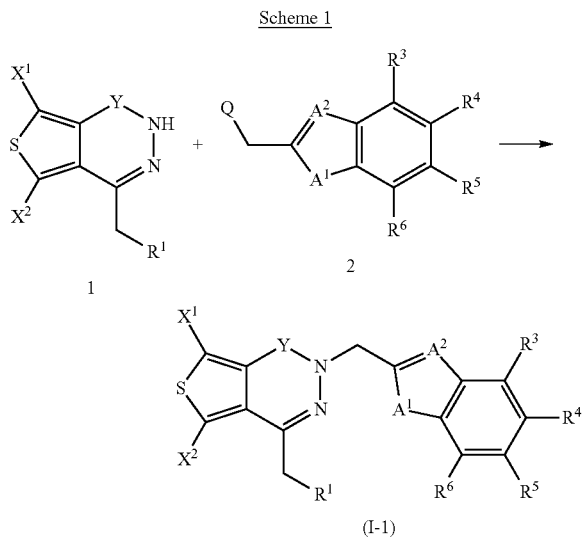

where $X^1$, $X^2$, $R^1$, $A^1$, $A^2$, $R^2$, $R^3$ through $R^7$ are defined as above and Q is a halogen, such as Cl, Br, I, and the like, or any other leaving group, such as $OSO_2Me$, OMs, OTs, OTf, and the like.

The compounds of Formula (I-2) can generally be prepared, for example, according to Scheme 2:

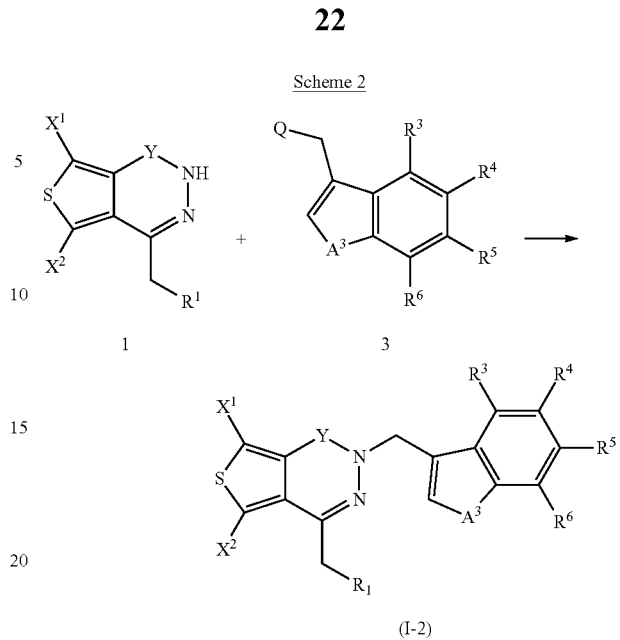

where $X^1$, $X^2$, $R^1$, $A^1$, $A^2$, $R^2$, $R^3$ through $R^7$ are defined as above and Q is a halogen, such as Cl, Br, I, and the like, or any other leaving group, such as $OSO_2Me$, OMs, OTs, OTf, and the like.

The compounds of Formula (I-3) can generally be prepared, for example, according to Scheme 3:

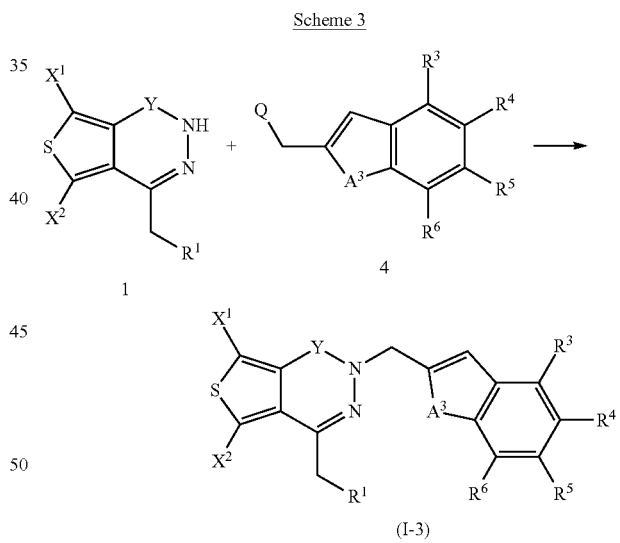

where $X^1$, $X^2$, $R^1$, $A^1$, $A^2$, $R^2$, $R^3$ through $R^7$ are defined as above and Q is a halogen, such as Cl, Br, I, and the like, or any other leaving group, such as $OSO_2Me$, OMs, OTs, OTf, and the like.

In certain embodiments, the reaction can be carried out in the presence of a base, such as potassium tert-butoxide, sodium hydride, sodium methoxide, sodium ethoxide, and the like.

In certain embodiments, the reaction can be carried out using aprotic solvents, such as DMF, THF, NMP, and the like. In certain embodiments, the reaction can be carried out using alcohol solvents, such as methanol, ethanol, and the like.

In certain embodiments, the reaction can be carried out at temperatures of between about 5° C. to about 80° C., such as 20° C. to 30° C.

In certain embodiments, the reaction can be subsequently followed by further separation and purification steps, such as chromatography (e.g., flash, HPLC, MPLC, etc.), crystallization, and the like.

The compounds of Formula (I-1) can also generally be prepared according to exemplary Scheme 4. Cyclic anhydride 5 is converted to compound 6 under acidic methanolysis conditions. Activation of the compound 6, followed by nucleophilic addition and decarboxylation provides ketoester 7. Treatment of compound 7 with hydrazine affords cyclized compound 8. Compound 8 is then coupled to compound 2 under basic conditions to provide a compound of formula 9. Deprotection or hydrolysis of compound 9 provides a compound of formula 10

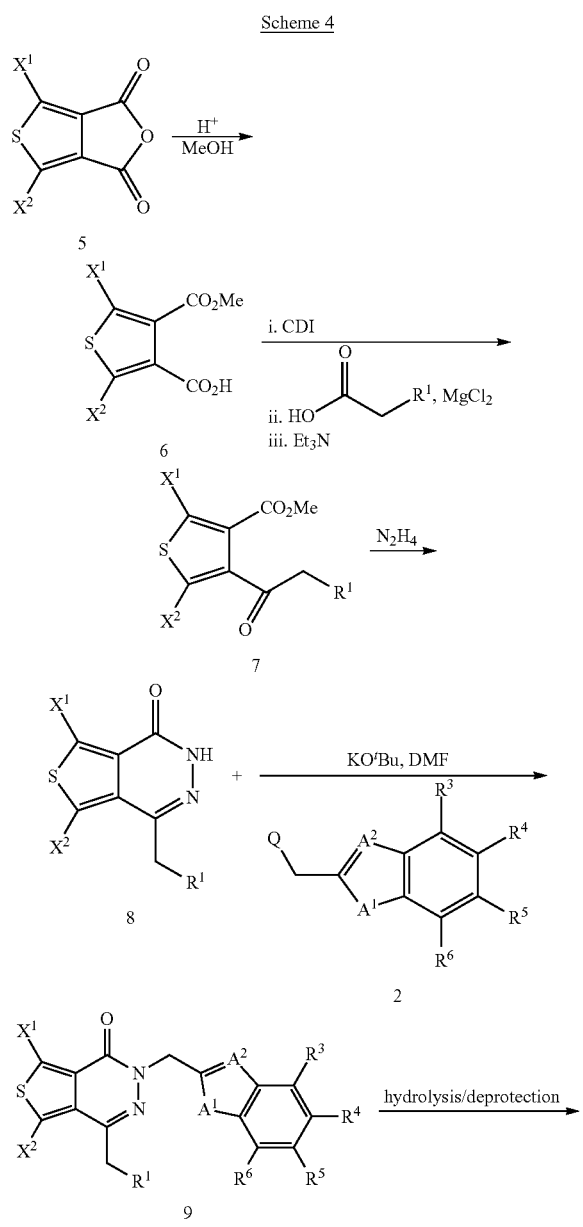

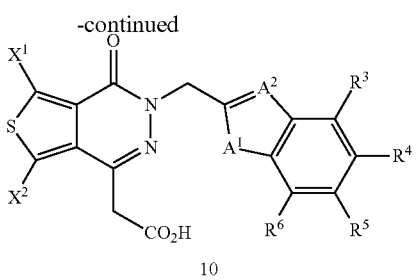

The compounds of Formula (I-2) can also generally be prepared according to Scheme 4, by replacing

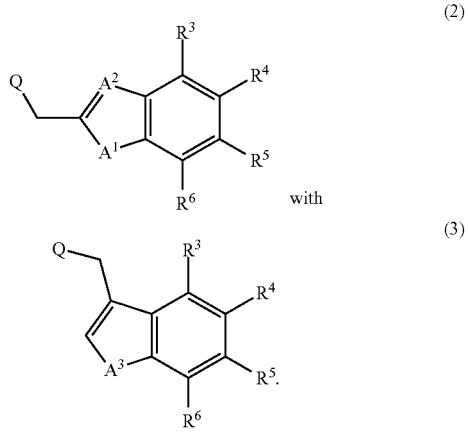

Similarly, the compounds of Formula (I-3) can also generally be prepared according to Scheme 4, by replacing

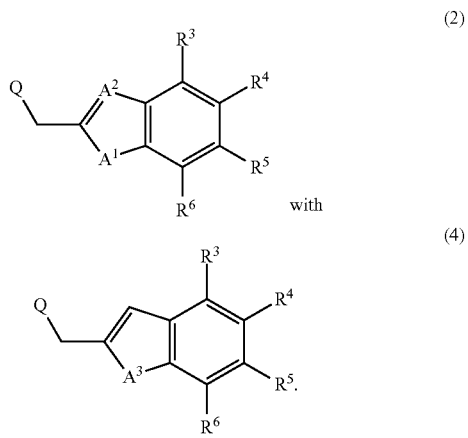

Other suitable reactions are possible, such as hydrolysis of the compound of Formula (I) in to obtain different forms of the compound of Formula (I-1), (I-2), or (I-3). For example, compounds having tert-butoxy, methoxy, ethoxy, and the like group as $R^2$ can be hydrolyzed by reacting with a suitable reagent, such as trifluoroacetic acid (TFA), HCl, KOH, or the like, to obtain a compound of Formula (I) having hydrogen as $R^2$.

For example, the following exemplary synthesis can be carried out according to Scheme 5.

Scheme 5

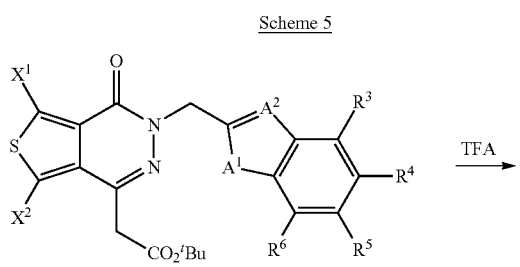

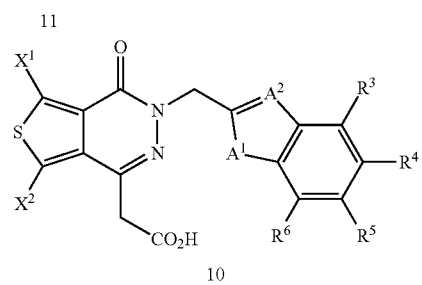

In some other embodiments, where Y is C=O, subsequent reactions can be carried out to replace C=O with C=S or C=N, or the like.

Compounds of Formula (2)

To obtain compounds of Formula (2), different possibilities exist. Compounds of Formula (2) can be synthesized by a variety of different reactions, such as a condensation reaction as schematically illustrated below in Scheme 6. The reaction can be carried out using a variety of solvents, such as ethanol, methanol, DMF, AcOH, and the like. The reaction can be carried out at temperatures of between about 5° C. to about 80° C., such as, for example, 55° C. to 65° C.

Scheme 6

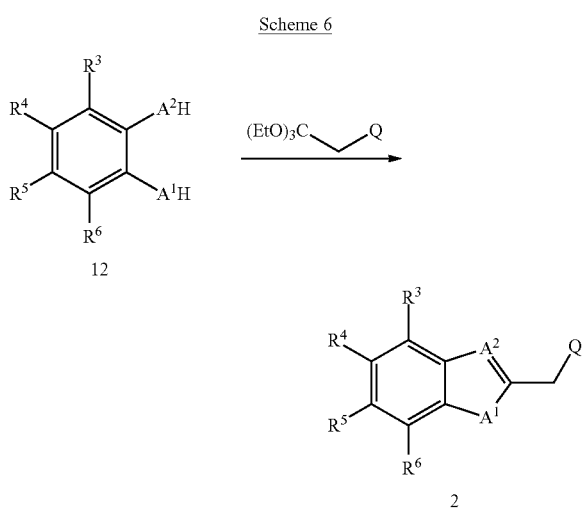

Additional exemplary descriptions regarding synthesis of certain compounds of Formula (2) are described in *J. Med. Chem.* (1991), Vol. 34, pp. 108-122; *J. Med. Chem.* (1992), Vol. 35, No. 3, pp. 457-465; and U.S. Pat. No. 8,916,563; each of which hereby incorporated by reference in its entirety.

Compounds of Formula (1)

To obtain compounds of Formula (1), different possibilities exist. For example, compounds of Formula (1) can be synthesized as shown in Scheme 7. For example, to obtain a compound of Formula (1) when Y is C=O, reaction of a compound represented by Formula (13) with a reagent that causes addition-cyclization reaction, such as hydrazine, can be carried out as shown in Scheme 7. The reaction can be carried out using a variety of solvents, such as ethanol, methanol, THF, and the like. The reaction can be carried out at temperatures of between about 20° C. to about 100° C., such as 60° C. to 80° C.

Scheme 7

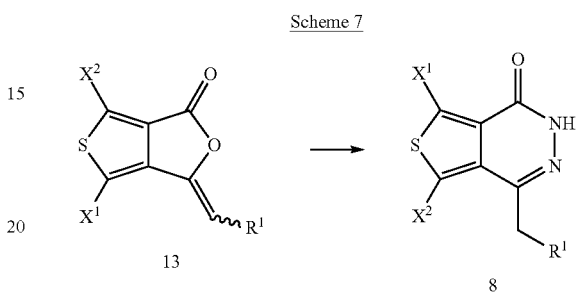

The compounds of Formula (13) can be obtained, for example, by a reaction of an anhydride with a reagent that causes a Wittig reaction, such as (tert-butoxycarbonylmethylene)-triphenylphosphorane, and the like, as shown in Scheme 8. The reaction can be carried out using aprotic solvents, such as $CH_2Cl_2$, THF, 1,4-dioxane, toluene, and the like. The reaction can be carried out at temperatures of between about 20° C. to about 110° C., such as 55° C. to 70° C.

Scheme 8

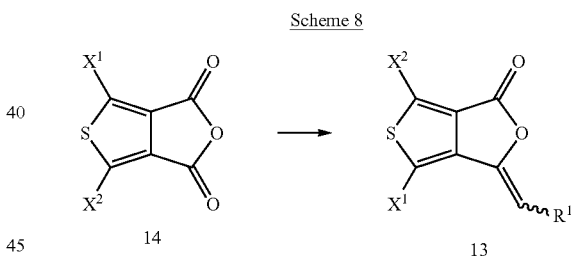

In certain embodiments, reaction of an anhydride, such as compound 15, with a reagent that causes a Wittig reaction can lead to a mixture of the particular compounds represented by 16 and 17, as exemplified below (Scheme 9). In such instances, if necessary, the mixture can be separated and purified to obtain the particular compounds of interest (e.g., compound 16 or 17).

Scheme 9

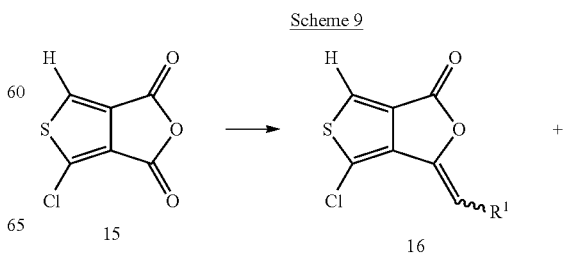

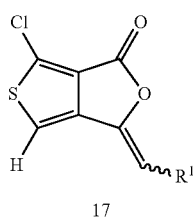

17

In certain embodiments, the compounds of Formula (13) can be obtained by the Perkins Reaction, as shown in Scheme 10. The Perkins reaction can employ KOAc/Ac$_2$O, as shown in Scheme 10. However, other temperatures and other bases, such as K$_2$CO$_3$ and the like can be utilized. Additional details of the Perkins reaction can be found in WO 03/061660, the contents of which are incorporated by reference herein in its entirety.

Scheme 10

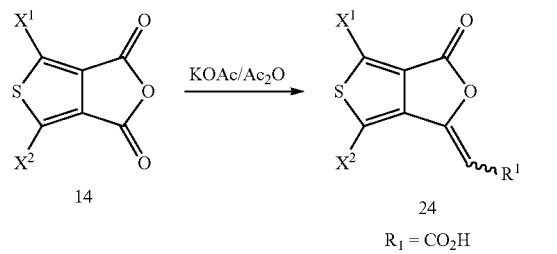

R$_1$ = CO$_2$H

The compounds of Formula (14) can be obtained by reaction of dicarboxylic acid derivative represented by Formula (18) with a suitable anhydride forming reagent, such as dicyclohexylcarbodiimide (DCC) or acetic anhydride, to obtain the compounds of Formula (14) as schematically illustrated below (Scheme 11). The reaction can be carried out using non-nucleophilic solvents, such as acetic anhydride, THF, and the like. The reaction can be carried out at temperatures of between about 20° C. to about 100° C., such as 60° C. to 80° C.

Scheme 11

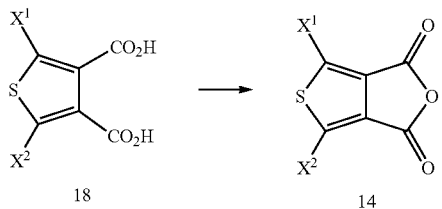

The compounds of Formula (14) can also be obtained as described by Ayres et al. in *Tetrahedron*, 1975, 31, 1755-1760 (hereby incorporated by reference in its entirety). The compounds of Formula (14) can be converted to compounds of formula (I) by known methods, e,g., as described previously in U.S. Pat. No. 8,916,563 (hereby incorporated by reference in its entirety).

The compounds of Formula (18) can generally be obtained through commercial sources, such as Sigma-Aldrich. Alternatively, compounds of Formula (18) can be obtained by reaction of a suitable precursor represented by Formula (19) or Formula (20) with a suitable dicarboxylic acid derivative forming reagent, such as NaMnO$_4$ and/or NaOH, to obtain the compounds of Formula (18) as schematically illustrated below (Schemes 12 and 13). The reaction can be carried out using aqueous solvents, such as water. The reaction can be carried out at temperatures of between about 50° C. to about 100° C., such as 85° C. to 95° C.

Scheme 12

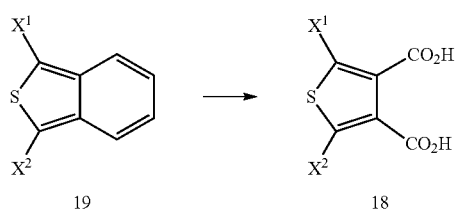

Scheme 13

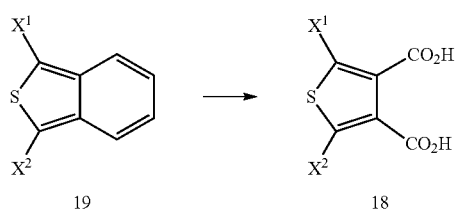

The compounds of Formula (18), where X$^1$ and X$^2$ are Cl, can be obtained as described by Ayres et al. in *Tetrahedron*, 1975, 31, 1755-1760 (hereby incorporated by reference in its entirety), as in shown in Scheme 14. Bis-iodination of compound 34 followed by transmetallation and carboxylation provides compound 36. Other halogenated derivatives can also be used as starting materials to provide compounds of Formula (18). Subsequent conversion of the di-carboxylic acid functional groups of compounds of Formula (18) to form a cyclic anhydride, as described above, provides compounds of Formula (14). Compounds of Formula (14) can be converted to compounds of formula (I) by known methods. Exemplary methods are described in U.S. Pat. No. 8,916,563 (hereby incorporated by reference in its entirety).

Scheme 14

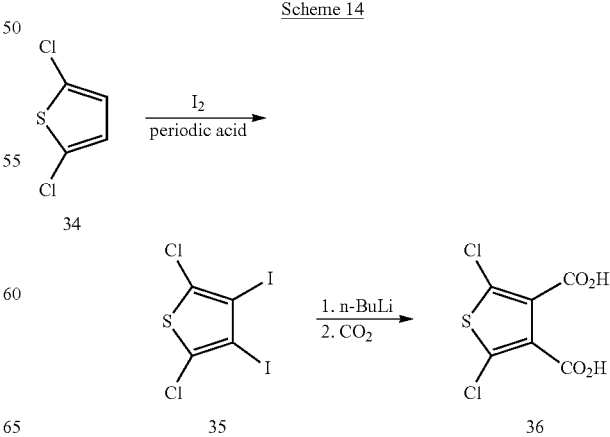

Additional Synthetic Schemes for Compound of Formula (I)

The synthetic schemes described above for preparing compounds of formula (I) are illustrative and are not meant to limit the possible techniques one skilled in the art may use to prepare compounds disclosed herein. Different methods will be evident to those skilled in the art. Additional reactions can be carried out for the synthesis of additional embodiments of compounds represented by formula (I).

To obtain compounds of Formula (I) where Y is C=S, the following synthesis can be carried out (Scheme 15). Treatment of compound 21 with Lawesson's reagent provides the corresponding thiocarbonyl derivative 22. Subsequent deprotection or hydrolysis provides compound 23.

Scheme 15

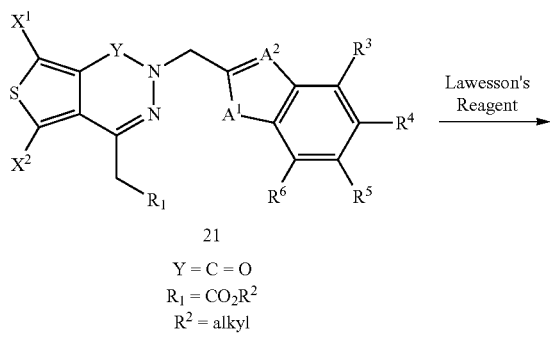

21
Y = C = O
$R_1 = CO_2R^2$
$R^2$ = alkyl

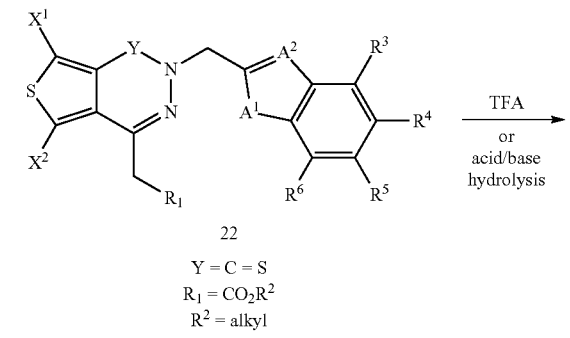

22
Y = C = S
$R_1 = CO_2R^2$
$R^2$ = alkyl

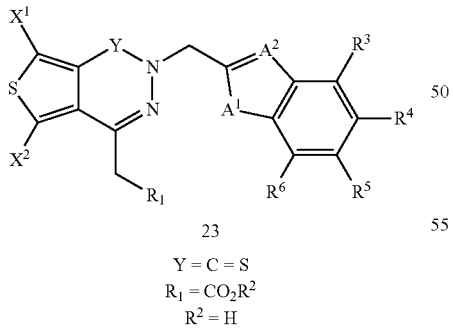

23
Y = C = S
$R_1 = CO_2R^2$
$R^2$ = H

To obtain compounds of Formula (I) where Y is C=NR*, wherein R* represents hydrogen or an alkyl substituent for example, the following synthesis can be carried out (Scheme 16).

Scheme 16

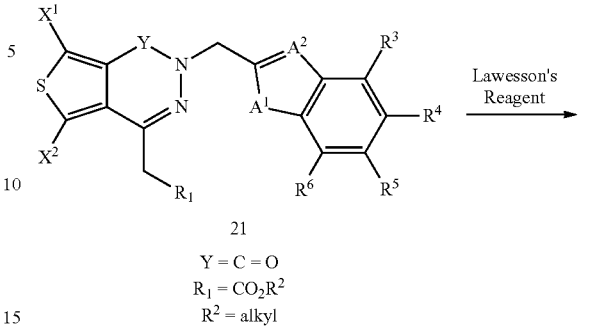

21
Y = C = O
$R_1 = CO_2R^2$
$R^2$ = alkyl

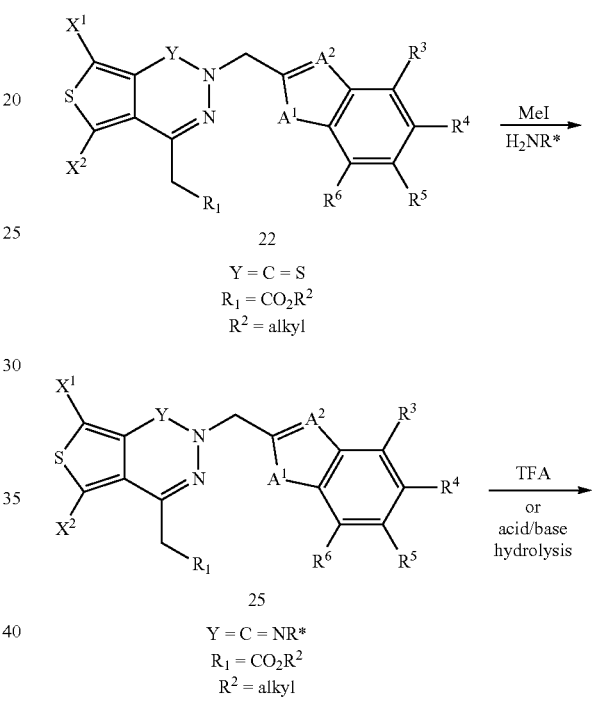

22
Y = C = S
$R_1 = CO_2R^2$
$R^2$ = alkyl

25
Y = C = NR*
$R_1 = CO_2R^2$
$R^2$ = alkyl

25
Y = C = NR*
$R_1 = CO_2R^2$
$R^2$ = H

Compounds of Formula (I) where Y is a covalent bond can be prepared as described previously in U.S. Pat. No. 8,916,563.

Other substitutions and modifications are further possible as would be apparent to one of ordinary skill in the art. For example, in Scheme 17, KOH can be utilized in place of NaOH. In Scheme 18 below, KO$^t$Bu can be used in place of NaH. Additionally, instead of DMF, NMP or THF can be utilized.

Scheme 17

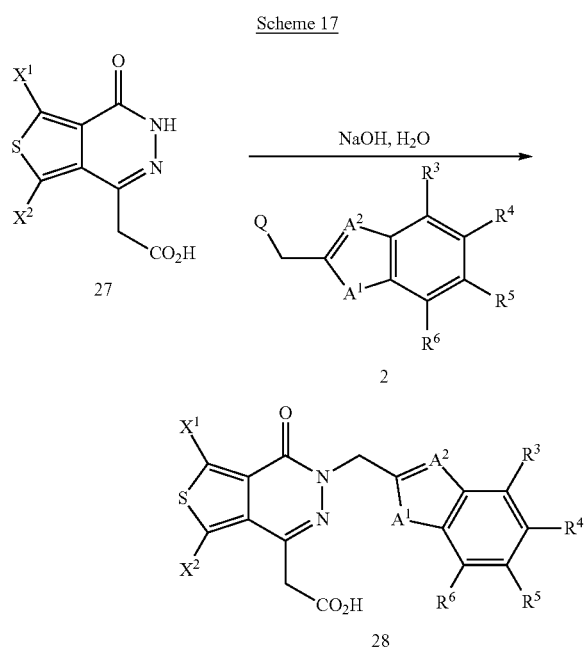

Scheme 18

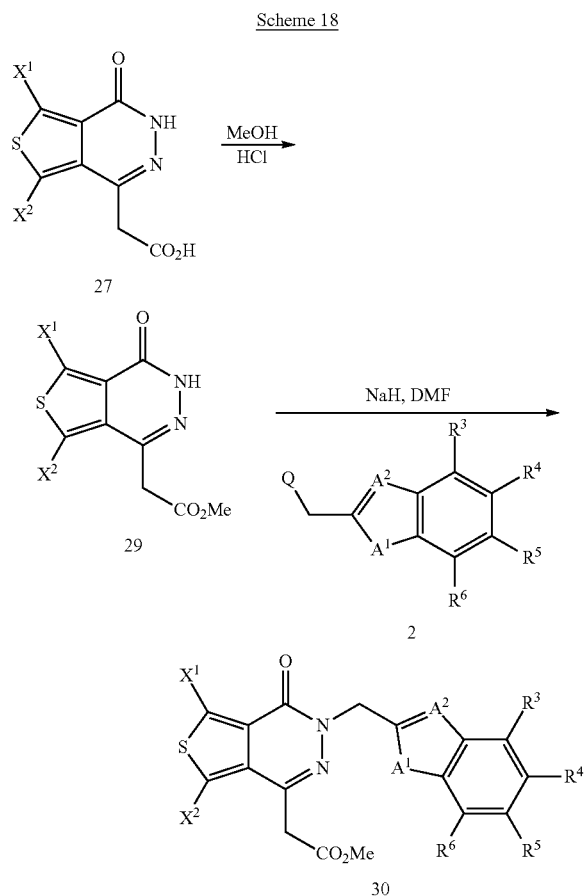

In certain embodiments, the following alternative synthesis can be carried out (Scheme 19).

Scheme 19

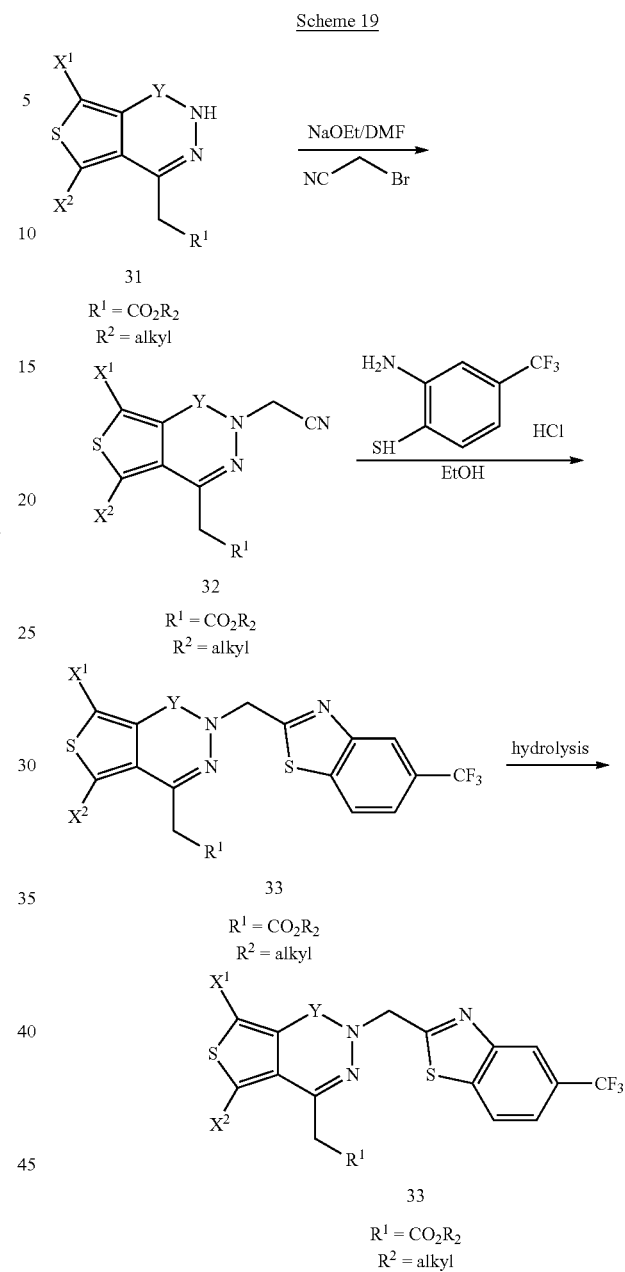

Compounds or compositions of the invention can be useful in applications that benefit from inhibition of aldose reductase enzymes. Exemplary utility of aldose reductase inhibition may be found, for example, in U.S. Pat. Nos. 8,916,563; 5,677,342; 5,155,259; 4,939,140; U.S. Publication Number US 2006/0293265; and Roy et al., in *Diabetes Research and Clinical Practice* 1990, 10(1), 91-97; and references cited therein; each of which hereby incorporated by reference in its entirety. Inhibition of aldose reductase also has been found to prevent metastasis of colon cancer and mitosis in colon cancer cells (See, for example, Tammali, R. et al., Inhibition of Aldose Reductase Prevents Colon Cancer Metastasis, *Carcinogenesis* 2011, doi: 10.1093/carcin/bgr102; published online: Jun. 3, 2011; *Angiogenesis* 2011 May; 14(2):209-21; and *Mol. Cancer Ther.* 2010, April; 9(4): 813-824; each of which hereby incorporated by reference in its entirety).

In certain embodiments, compounds and/or compositions of the invention can be useful in promoting healthy aging of skin, the treatment of skin disorders, the treatment of angiogenesis disorders such as cancers, including colon cancer, the treatment of non-cardiac tissue damage, the treatment of cardiovascular disorders, the treatment of renal disorders, the treatment of evolving myocardial infarction, the treatment of ischemic injury, and the treatment various other disorders, such as complications arising from diabetes. Such disorders can include, but are not limited to, atherosclerosis, coronary artery disease, diabetic nephropathy, diabetic neuropathy, diabetic retinopathy, infections of the skin, peripheral vascular disease, stroke, asthma and the like.

In certain embodiments, compounds and/or compositions of the invention can be useful in cardiovascular applications. For example, compounds and/or compositions of the invention can be used to treat patients undergoing a heart bypass surgery to improve recovery after the surgery. In another example, compounds and/or compositions of the invention can be used to inhibit or reduce accumulation or rapid onset of atherosclerotic plaque.

In some other embodiments, compounds and/or compositions of the invention can be useful in topical applications. For example, compounds and/or compositions of the invention can be used to retard or reduce skin aging.

In certain embodiments, compounds of Formula (I) can be administered to a subject in need of treatment at dosages ranging from about 0.5 to about 25 mg/kg body weight of the subject to be treated per day, such as from about 1.0 to 10 mg/kg. However, additional variations are within the scope of the invention.

The compound of Formula (I) can be administered alone or in combination with pharmaceutically acceptable carriers, such as diluents, fillers, aqueous solution, and even organic solvents. The compound and/or compositions of the invention can be administered as a tablet, powder, lozenge, syrup, injectable solution, and the like. Additional ingredients, such as flavoring, binder, excipients, and the like are within the scope of the invention.

In certain embodiments, pharmaceutically acceptable compositions can contain a compound of Formula (I) and/or a pharmaceutically acceptable salt thereof at a concentration ranging from about 0.01 to about 2 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

Other equivalent modes of administration can be found in U.S. Pat. No. 4,939,140, hereby incorporated by reference herein in its entirety.

In one embodiment, the present invention provides for the use of pharmaceutical compositions and/or medicaments comprised of a compound of Formula (I), or a pharmaceutically acceptable salt, hydrate, solvate, or pro-drug thereof, in a method of treating a disease state, and/or condition caused by or related to aldose reductase.

In another embodiment, the method of treatment comprises the steps of: (i) identifying a subject in need of such treatment; (ii) providing a compound of Formula (I), or a pharmaceutically acceptable salt, hydrate, solvate, or pro-drug thereof; and (iii) administering said compound of Formula (I) in a therapeutically effective amount to treat, suppress and/or prevent the disease state or condition in a subject in need of such treatment.

In another embodiment, the method of treatment comprises the steps of: (i) identifying a subject in need of such treatment; (ii) providing a composition comprising a compound of Formula (I), or a pharmaceutically acceptable salt, hydrate, solvate, or pro-drug thereof; and (iii) administering said composition in a therapeutically effective amount to treat, suppress and/or prevent the disease state or condition in a subject in need of such treatment.

In one embodiment, the subject in need is an animal. In another embodiment, the patient in need is an animal. Animals include all members of the animal kingdom, but are not limited to humans, mice, rats, cats, monkeys, dogs, horses, and swine. In some embodiments, the subject in need is a human. In some embodiments, the subject in need is a mouse, a rat, a cat, a monkey, a dog, a horse, or a pig. In some embodiments, the patient in need is a human. In some embodiments, the patient in need is a mouse, a rat, a cat, a monkey, a dog, a horse, or a pig.

In one embodiment, the compound or composition is administered orally. In another embodiment, the compound or composition is administered intravenously.

In one embodiment, the methods comprise administering to the subject an effective amount of a compound of Formula (I), or a pharmaceutically acceptable salt, solvate, hydrate or pro-drug thereof; or a composition comprising a compound of Formula (I), or a pharmaceutically acceptable salt, solvate, hydrate or pro-drug thereof, and a pharmaceutically acceptable carrier.

Pharmaceutically acceptable carriers are well-known to those skilled in the art, and include, for example, adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, for example, water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remin on's: The Science and Practice of Pharmacy, 22nd Ed. (Allen, Loyd V., Jr ed., Pharmaceutical Press (2012)); Modern Pharmaceutics, $5^{th}$ Ed. (Alexander T. Florence, Juergen Siepmann, CRC Press (2009)); Handbook of Pharmaceutical Excipients, $7^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In one embodiment, a pharmaceutical composition is a mixture of one or more of the compounds described herein, or pharmaceutically acceptable salts, solvates, pro-drugs or hydrates thereof, with other chemical components, such as physiologically acceptable carriers and excipients. The purpose of a pharmaceutical composition is to facilitate administration of a compound to an organism or subject.

In another embodiment, the method of treatment, prevention and/or suppression of a condition related to aldose reductase comprises the steps of: (i) identifying a subject in need of such treatment; (ii) providing a compound of Formula (I), or a pharmaceutically acceptable salt, solvate, hydrate or pro-drug thereof; or a composition comprising a compound of Formula (I), or a pharmaceutically acceptable salt, solvate, hydrate or pro-drug thereof, and a pharmaceutically acceptable carrier; and (iii) administering said compound or composition in a therapeutically effective amount to treat, prevent and/or suppress the disease state or condition related to aldose reductase in a subject in need of such treatment.

A "pro-drug" or "pro-drug" refers to an agent which is converted into the active drug in vivo. Pro-drugs are often useful because, in some situations, they are easier to administer than the parent drug. They are bioavailable, for instance, by oral administration whereas the parent drug is either less bioavailable or not bioavailable. In some embodiments, the pro-drug has improved solubility in pharmaceutical compositions over the parent drug. For example, the compound carries protective groups that are removed in vivo, thus releasing active compound. The term "pro-drug" may apply to such functionalities as, for example, the acid functionalities of the compounds of Formula (I). Pro-drugs may be comprised of structures wherein an acid group is masked, for example, as an ester or amide. Further examples of pro-drugs are discussed herein and, for example, by Alexander et al., *J. Med. Chem.* 1988, 31, 318 (hereby incorporated by reference in its entirety).

In one embodiment, the present invention also encompasses methods comprising pro-drugs of compounds of Formula (I) and/or pharmaceutical compositions thereof. Pro-drugs include derivatives of compounds that can hydrolyze, oxidize, or otherwise react under biological conditions (in vitro or in vivo) to provide an active compound of the invention. Examples of pro-drugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, and biohydrolyzable phosphate analogues. Pro-drugs may be comprised of structures wherein a acid group is masked, for example, as an ester or amide. Further examples of pro-drugs are discussed, for example, by Alexander et al., *J. Med. Chem.* 1988, 31, 318; and in *The Practice of Medicinal Chemistry* (Camille Wermuth, ed., 1999, Academic Press; hereby incorporated by reference in its entirety). Pro-drugs are often useful because, in some situations, they are easier to administer than the parent drug. They are bioavailable, for instance, by oral administration whereas the parent drug is either less bioavailable or not bioavailable. In some embodiments, the pro-drug has improved solubility in pharmaceutical compositions over the parent drug. For example, the compound carries protective groups that are removed in vivo, thus releasing active compound.

In certain embodiments, pro-drugs of compounds with carboxyl functional groups are the $(C_1-C_4)$ alkyl esters of the carboxylic acid. The carboxylate esters are conveniently formed by esterifying any of the carboxylic acid moieties present on the molecule. Pro-drugs can typically be prepared using well-known methods, such as those described by *Burger's Medicinal Chemistry and Drug Discovery* $6^{th}$ ed. (Donald J. Abraham ed., 2001, Wiley) and *Design and Application of Pro-drugs* (H. Bundgaard ed., 1985, Harwood Academic Publishers Gmfh; each of which hereby incorporated by reference in its entirety). Biohydrolyzable moieties of a compound of Formula (I) (i) do not interfere with the biological activity of the compound but can confer upon that compound advantageous properties in vivo, such as uptake, duration of action, or onset of action; or (ii) may be biologically inactive but are converted in vivo to the biologically active compound. Examples of biohydrolyzable esters include, but are not limited to, $(C_1-C_4)$ alkyl esters, alkoxyacyloxy esters, alkyl acylamino alkyl esters, and choline esters. Examples of biohydrolyzable amides include, but are not limited to, $(C_1-C_4)$ alkyl amides, α-amino acid amides, alkoxyacyl amides, and alkylaminoalkylcarbonyl amides. Examples of biohydrolyzable carbamates include, but are not limited to, $(C_1-C_4)$ alkylamines, substituted ethylenediamines, aminoacids, hydroxyalkylamines, heterocyclic and heteroaromatic amines, and polyether amines. In some embodiments, the biohydrolyzable moiety is a $(C_1-C_4)$ alkyl ester, an alkoxyacyloxy ester, an alkyl acylamino alkyl ester, or a choline ester. In some embodiments, the biohydrolyzable moiety is a $(C_1-C_4)$ alkyl ester, an alkoxyacyloxy ester, or an alkyl acylamino alkyl ester. In some embodiments, the biohydrolyzable moiety is a $(C_1-C_4)$ alkyl ester or an alkoxyacyloxy ester. In some embodiments, the biohydrolyzable moiety is a $(C_1-C_4)$ alkyl ester. In some embodiments, the biohydrolyzable moiety is a $(C_1-C_3)$ alkyl ester. In some embodiments, the biohydrolyzable moiety is a methyl ester or an ethyl ester. In some embodiments, the biohydrolyzable moiety is a t-butyl ester. In some embodiments, the biohydrolyzable moiety is a $(C_1-C_4)$ alkyl amide, an α-amino acid amide, an alkoxyacyl amide, or an alkylaminoalkylcarbonyl amide. In some embodiments, the biohydrolyzable moiety is a $(C_1-C_4)$ alkyl amide, an α-amino acid amide, or an alkoxyacyl amide. In some embodiments, the biohydrolyzable moiety is a $(C_1-C_4)$ alkyl amide or an α-amino acid amide. In some embodiments, the biohydrolyzable moiety is a $(C_1-C_4)$ alkyl amide.

In some embodiments, the biohydrolyzable moiety is a $(C_1-C_4)$ alkyl amine, a substituted ethylenediamine, an aminoacid, a hydroxyalkylamine, a heterocyclic amine, a heteroaromatic amine, or a polyether amine. In some embodiments, the biohydrolyzable moiety is a $(C_1-C_4)$ alkyl amine, an aminoacid, a hydroxyalkylamine, a heterocyclic amine, a heteroaromatic amine, or a polyether amine. In some embodiments, the biohydrolyzable moiety is a $(C_1-C_4)$ alkyl amine, an aminoacid, a hydroxyalkylamine, or a polyether amine. In some embodiments, the biohydrolyzable moiety is a $(C_1-C_4)$ alkyl amine, an aminoacid, or a hydroxyalkylamine. In some embodiments, the biohydrolyzable moiety is a $(C_1-C_4)$ alkyl amine.

In one embodiment, the compounds of the invention are formulated into pharmaceutical compositions for administration to subjects in a biologically compatible form suitable for administration in vivo. According to another aspect, the present invention provides a pharmaceutical composition comprising a compound of Formula (I) in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In one embodiment, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, for example, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^-R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, the compound of Formula (I) and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present invention are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present invention are administered to a human or animal subject by known procedures including oral administration, sublingual or buccal administration. In one embodiment, the compound and/or composition is administered orally.

For oral administration, a formulation of the compounds of the invention may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, for example, sweetening agents such as fructose, aspartame or saccharin; flavoring agents such as peppermint, oil of wintergreen, or cherry; coloring agents; and preservative agents, to provide a pharmaceutically palatable preparation.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In accordance with the methods of the present invention, the compounds of the invention are administered to the subject in a therapeutically effective amount, for example to reduce or ameliorate symptoms related to aldose reductase activity in the subject. This amount is readily determined by the skilled artisan, based upon known procedures, including analysis of titration curves established in vivo and methods and assays disclosed herein.

In one embodiment, the methods comprise administration of a therapeutically effective dosage of the compounds of the invention. In some embodiments, the therapeutically effective dosage is at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each patient's circumstances. In specific embodiments of the invention, suitable dose ranges for oral administration of the compounds of the invention are generally about 1 mg/day to about 1000 mg/day. In one embodiment, the oral dose is about 1 mg/day to about 800 mg/day. In one embodiment, the oral dose is about 1 mg/day to about 500 mg/day. In another embodiment, the oral dose is about 1 mg/day to about 250 mg/day. In another embodiment, the oral dose is about 1 mg/day to about 100 mg/day. In another embodiment, the oral dose is about 5 mg/day to about 50 mg/day. In another embodiment, the oral dose is about 5 mg/day. In another embodiment, the oral dose is about 10 mg/day. In another embodiment, the oral dose is about 20 mg/day. In another embodiment, the oral dose is about 30 mg/day. In another embodiment, the oral dose is about 40 mg/day. In another embodiment, the oral dose is about 50 mg/day. In another embodiment, the oral dose is about 60 mg/day. In another embodiment, the oral dose is about 70 mg/day. In another embodiment, the oral dose is about 100 mg/day. It will be recognized that any of the dosages listed herein may constitute an upper or lower dosage range, and may be combined with any other dosage to constitute a dosage range comprising an upper and lower limit.

Any of the compounds and/or compositions of the invention may be provided in a kit comprising the compounds and/or compositions. Thus, in one embodiment, the compound and/or composition of the invention is provided in a kit.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples serve to illustrate the exemplary modes of making and practicing the invention. However, the scope of the invention is not to be construed as limited to specific embodiments disclosed in these Examples, which are illustrative only.

Example 1: Preparation of Compound VII

Compound VII was prepared as schematically illustrated below.

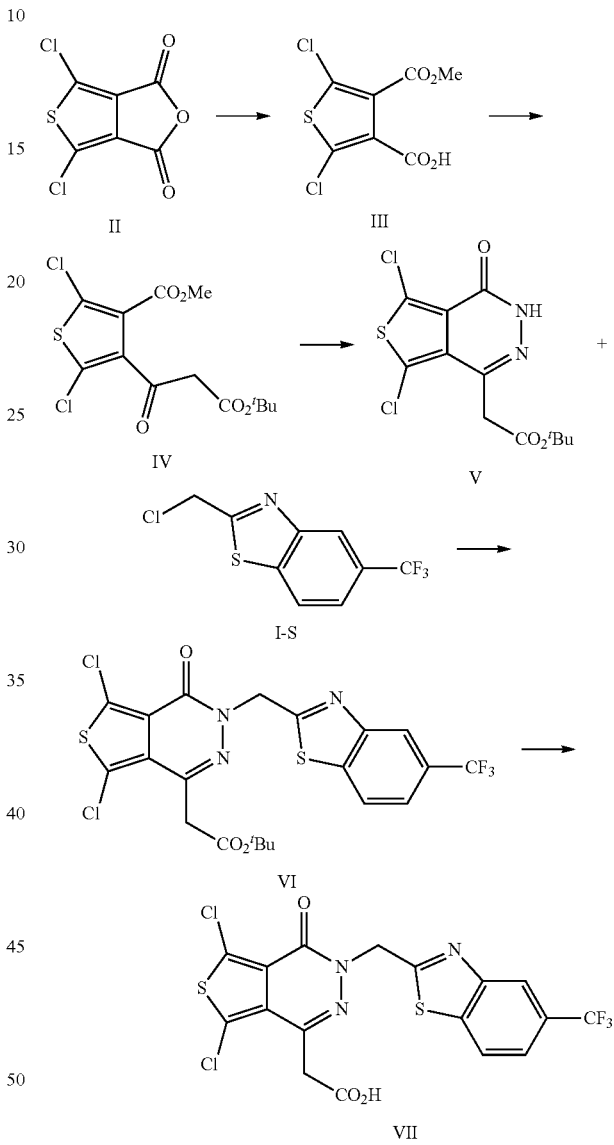

2-(chloromethyl)-5-(trifluoromethyl)benzo[d]thiazole (Compound I-S)

Compound I-S was prepared using the same method described previously in U.S. Pat. No. 8,916,563.

4,6-dichloro-1H,3H-thieno[3,4-c]furan-1,3-dione (Compound II)

Compound II was prepared using the same method described previous in Ayres, B. E., Longworth, S. W., McOmie, J. F. W. *Tetrahedron*, 1975, 31, 1755-1760.

2,5-dichloro-4-(methoxycarbonyl)thiophene-3-carboxylic Acid (Compound III)

A solution of 0.495 g (2.22 mmol) of 4,6-dichloro-1H,3H-thieno[3,4-c]furan-1,3-dione (Compound II) in 4.0 mL of MeOH was treated with TFA (1 drop) and heated to 65° C. overnight. The reaction mixture was cooled to ambient temperature and concentrated in vacuo. To the obtained residue was added ether followed by saturated aqueous NaHCO$_3$. The layers were separated and the aqueous layer was extracted with ether (1×). The aqueous layer was then acidified to pH=2 by addition of conc. HCl. The aqueous layer was extracted with EtOAc (3×) and the combined organics from the second extraction washed with brine (1×). The organic layer was dried over Na$_2$SO$_4$, filtered and concentrated in vacuo to yield 0.537 g (95% crude yield) of 2,5-dichloro-4-(methoxycarbonyl)thiophene-3-carboxylic acid (Compound III) as a white solid that was used without further purification: $^1$H NMR (CDCl$_3$, 400 MHz): $\delta_{ppm}$ 3.91 (s, 3H); $^{13}$C NMR (CDCl$_3$, 100 MHz): $\delta_{ppm}$ 165.6, 162.0, 133.9, 131.0, 129.6, 128.1, 53.0.

Methyl 4-(3-(tert-butoxy)-3-oxopropanoyl)-2,5-dichlorothiophene-3-carboxylate (Compound IV)

In a first flask, a solution of 0.537 g (2.11 mmol) of Compound III in 8.0 mL of DMF was treated slowly with 0.393 g (2.42 mmol) of CDI. The reaction mixture was stirred at ambient temperature for 2 hours. In a separate second flask, to a solution of 0.439 g (2.74 mmol) of mono-tert-butyl malonate in 8.0 mL of DMF cooled to 0° C. was added 0.261 g (2.74 mmol) of MgCl$_2$. After stirring at 0° C. for 5 minutes, 1.2 mL (8.42 mmol) of triethylamine was added and the resulting reaction mixture stirred at ambient temperature for 2 hours. After 2 hours, the content of flask #1 was added to flask #2 and the combined reaction mixture stirred at ambient temperature overnight. Subsequently, the reaction mixture was cooled to 0° C. and treated with aqueous 1.0 M HCl and stirred for 20 minutes. The mixture was extracted with ether (3×) and washed sequentially with water (2×) and brine (1×). The organic layer was dried over Na$_2$SO$_4$, filtered and concentrated in vacuo to yield crude material 0.170 g (23% crude yield) of methyl 4-(3-(tert-butoxy)-3-oxopropanoyl)-2,5-dichlorothiophene-3-carboxylate (Compound IV) that was used without further purification.

Tert-butyl 2-(5,7-dichloro-4-oxo-3,4-dihydrothieno[3,4-d]pyridazin-1-yl)acetate (Compound V)

To 0.170 g (0.482 mmol) of Compound IV in 4.0 mL of MeOH was added 17 µL (0.530 mmol) of hydrazine. The resulting reaction mixture was stirred at ambient temperature for 2 hours. Subsequently, the reaction mixture was concentrated in vacuo and the residue purified via flash column chromatography over silica gel (monitored by thin layer chromatography) and eluted with 2:1 (v/v) hexanes:ethyl aceate. Evaporation of the collected fractions yielded 0.091 g (57% yield) of tert-butyl 2-(5,7-dichloro-4-oxo-3,4-dihydrothieno[3,4-d]pyridazin-1-yl)acetate (Compound V) as a white solid: $^1$H NMR (CDCl$_3$, 400 MHz): $\delta_{ppm}$ 9.15 (br s, 1H), 3.89 (s, 2H), 1.46 (s, 9H).

Tert-butyl 2-(5,7-dichloro-4-oxo-3-(5-(trifluoromethyl)benzo[d]thiazol-2-yl)methyl)-3,4-dihydrothieno[3,4-c]pyridazin-1-yl)acetate (Compound VI)

To a solution of 0.091 g (0.271 mmol) of Compound V in 3.0 mL of DMF was added 0.037 g (0.326 mmol) of KO$^t$Bu. The resulting dark mixture was stirred at ambient temperature for 10 minutes before 0.082 g (0.326 mmol) of 2-(chloromethyl)-5-(trifluoromethyl)benzo[d]thiazole (Compound I-S) was added. After the reaction mixture stirred at ambient temperature for 2 hours, the reaction mixture was partitioned between water and ether, the layers separated, and the aqueous layer extracted with ether (2×). The combined ethereal layers were washed sequentially with saturated aqueous NaHCO$_3$ (1×), water (1×), 1.0M aqueous HCl (1×), and brine (1×). The organic layer was dried over Na$_2$SO$_4$, filtered and concentrated in vacuo. The obtained residue was purified via flash column chromatography over silica gel (monitored by thin layer chromatography) and eluted with 4:1 (v/v) hexanes:ethyl acetate. Evaporation of the collected fractions yielded 0.072 g (48% yield) of tert-butyl 2-(5,7-dichloro-4-oxo-3-((5-(trifluoromethyl)benzo[d]thiazol-2-yl)methyl)-3,4-dihydrothieno[3,4-d]pyridazin-1-yl)acetate (Compound VI): $^1$H NMR (CDCl$_3$, 400 MHz): $\delta_{ppm}$ 8.28 (s, 1H), 7.94 (d, J=8.4 Hz, 1H), 7.60 (d, J=8.4 Hz, 1H), 5.63 (s, 2H), 3.92 (s, 2H), 1.45 (s, 9H); MS ESI (m/z) 550 (M+1)$^+$.

2-(5,7-dichloro-4-oxo-3-((5-(trifluoromethyl)benzo[d]thiazol-2-yl)methyl)-3,4-dihydrothieno[3,4-d]pyridazin-1-yl)acetic Acid (Compound VII)

To a solution of 0.072 g (0.131 mmol) of Compound VI in 1.0 mL of THF was added 5.0 mL of formic acid (88% in water) and 0.5 mL of water. The reaction mixture was stirred for 12 hours at ambient temperature. The reaction mixture was concentrated in vacuo and the residue partitioned between ether and saturated aqueous NaHCO$_3$. The layers were separated and the aqueous layer acidified to pH 2 by addition of conc. HCl. The precipitated solid was collected via filtration to yield 8 mg (12% yield) of 2-(5,7-dichloro-4-oxo-3-((5-(trifluoromethyl)benzo[d]thiazol-2-yl)methyl)-3,4-dihydrothieno[3,4-d]pyridazin-1-yl)acetic acid (Compound VII) as a white solid: m.p.=205-207° C. (not recrystallized); $^1$H NMR (acetone, 400 MHz): $\delta_{ppm}$ 8.32-8.28 (m, 2H), 7.75 (d, J=7.6 Hz, 1H), 5.67 (s, 2H), 4.04 (s, 2H); MS ESI (m/z) 494 (M+1)$^+$.

Example 2: Preparation of Compound XII

Compound XII was prepared as schematically illustrated below.

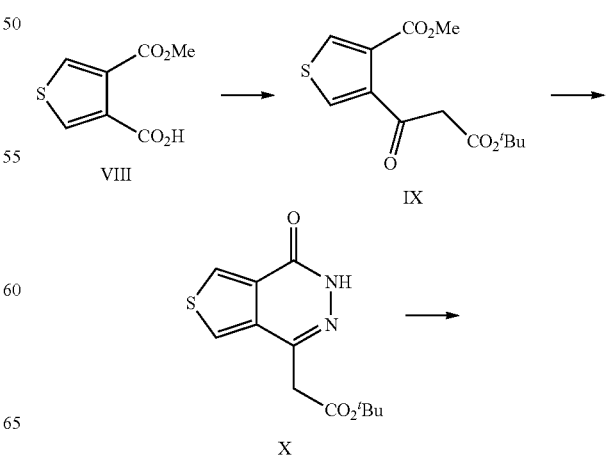

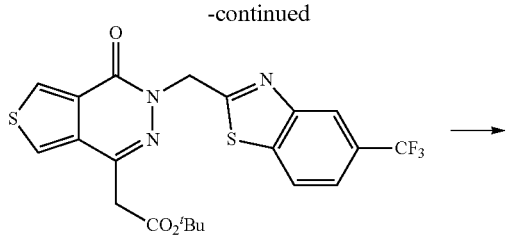

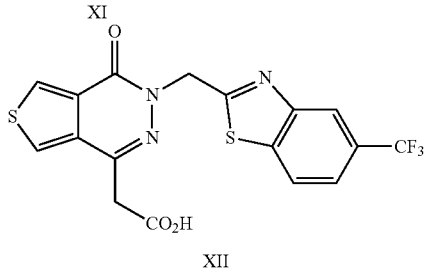

4-(methoxycarbonyl)thiophene-3-carboxylic Acid (Compound VIII)

Compound VIII was prepared using the same method described previous in Hawker, D. D., Silverman, R. B. *Bioorg. Med. Chem.*, 2012, 20, 5763-5773.

Methyl 4-(3-(tert-butoxy)-3-oxopropanoyl)thiophene-3-carboxylate (Compound IX)

In a first flask, a solution of 5.27 g (28.31 mmol) of Compound VIII in 35 mL of NMP was treated slowly with 5.28 g (32.55 mmol) of CDI. The reaction mixture was stirred at ambient temperature for 2 hours. In a separate second flask, to a solution of 5.67 g (35.39 mmol) of mono-tert-butyl malonate in 50 mL of NMP cooled to 0° C. was added 3.37 g (35.39 mmol) of $MgCl_2$. After stirring at 0° C. for 5 minutes, 14.8 mL (84.93 mmol) of N,N-diisopropylamine was added and the resulting reaction mixture stirred at ambient temperature for 2 hours. After 2 hours, the content of flask #1 was added to flask #2 and the combined reaction mixture stirred at ambient temperature overnight. Subsequently, the reaction mixture was cooled to 0° C. and treated with aqueous 1.0 M HCl and stirred for 20 minutes. The mixture was extracted with ether (3×) and washed sequentially with water (2×) and brine (1×). The organic layer was dried over $Na_2SO_4$, filtered and concentrated in vacuo. The residue was dissolved in 10 mL of ethyl acetate and 110 mL of hexanes was added. Stirred for 10 minutes and the solid precipitate was filtered off. Concentrated the filtrate in vacuo and the crude methyl 4-(3-(tert-butoxy)-3-oxopropanoyl)thiophene-3-carboxylate (Compound IX) was carried on without further purification.

Tert-butyl 2-(4-oxo-3,4-dihydrothieno[3,4-d]pyridazin-1-yl)acetate (Compound X)

To a solution of 8.04 g (28.31 mmol) of crude Compound IX in 70 mL of MeOH at 0° C. was added 2.7 mL (42.46 mmol) of hydrazine hydrate (50-60% in $H_2O$). The resulting reaction mixture was stirred at 0° C. for 2 hours. Diluted the reaction mixture with water and the precipitated solid was collected via filtration to yield 2.99 g (40% yield over two steps) of tert-butyl 2-(4-oxo-3,4-dihydrothieno[3,4-d]pyridazin-1-yl)acetate (Compound X) as a white solid: $^1$H NMR ($CDCl_3$, 400 MHz): $\delta_{ppm}$ 9.29 (br s, 1H), 8.44 (d, J=2.4 Hz, 1H), 7.83 (d, J=2.4 Hz, 1H), 3.76 (s, 2H), 1.44 (s, 9H); $^{13}$C NMR ($CDCl_3$, 100 MHz): $\delta_{ppm}$ 168.5, 158.0, 139.2, 133.3, 130.7, 129.3, 123.9, 82.1, 40.9, 27.9; ESI (m/z) 308 $(M+MeCN)^+$.

Tert-butyl 2-(4-oxo-3-((5-(trifluoromethyl)benzo[d]thiazol-2-yl)methyl)-3,4-dihydrothieno[3,4-c]pyridazin-1-yl)acetate (Compound XI)

To a solution of 0.100 g (0.376 mmol) of Compound X in 2.5 mL of DMF was added 0.044 g (0.391 mmol) of KO$^t$Bu. The resulting dark mixture was stirred at ambient temperature for 15 minutes before 0.104 g (0.414 mmol) of Compound I-S was added. After the reaction mixture stirred at ambient temperature for 2 hours, the reaction mixture was partitioned between water and ether, the layers separated, and the aqueous layer extracted with ether (2×). The combined ethereal layers were washed sequentially with 1.0M NaOH (1×), water (1×), 1.0M aqueous HCl (1×), and brine (1×). The organic layer was dried over $Na_2SO_4$, filtered and concentrated in vacuo. The obtained residue was purified via flash column chromatography over silica gel (monitored by thin layer chromatography) and eluted with 2:1 (v/v) hexanes:ethyl acetate. Evaporation of the collected fractions yielded 0.058 g (32% yield) of tert-butyl 2-(4-oxo-3-((5-(trifluoromethyl)benzo[d]thiazol-2-yl)methyl)-3,4-dihydrothieno[3,4-d]pyridazin-1-yl)acetate (Compound XI):: $^1$H NMR ($CDCl_3$, 400 MHz): $\delta_{ppm}$ 8.45 (d, J=3.2 Hz, 1H), 8.29 (s, 1H), 7.91 (d, J=8.8 Hz, 1H), 7.83 (d, J=3.2 Hz, 1H), 7.59 (d, J=8.8 Hz, 1H), 5.75 (s, 2H), 3.78 (s, 2H), 1.41 (s, 9H); ESI (m/z) 482 $(M+H)^+$.

2-(4-oxo-3-((5-(trifluoromethyl)benzo[d]thiazol-2-yl)methyl)-3,4-dihydrothieno[3,4-d]pyridazin-1-yl)acetic acid (Compound XII): A solution of 0.058 g (0.121 mmol) of Compound XI in 1.0 mL of trifluoroacetic acid and 1.0 mL of $CH_2Cl_2$ was stirred at ambient temperature for 2 hours. The reaction mixture was concentrated in vacuo and the residue partitioned between ether and saturated aqueous $NaHCO_3$. The layers were separated and the ethereal layer washed with saturated aqueous $NaHCO_3$ (1×). The aqueous layer was acidified to pH=2 by addition of conc. HCl and the precipitated solid was collected via filtration to yield 20 mg (39% yield) of 2-(4-oxo-3-((5-(trifluoromethyl)benzo[d]thiazol-2-yl)methyl)-3,4-dihydrothieno[3,4-d]pyridazin-1-yl)acetic acid (Compound XII) as a white solid: m.p.=174-176° C. (not recrystallized); $^1$H NMR (acetone, 400 MHz): $\delta_{ppm}$ 8.60 (d, J=3.2 Hz, 1H), 8.33 (d, J=3.2 Hz, 1H), 8.29 (s, 1H), 8.26 (d, J=8.8 Hz, 1H), 7.74 (d, J=8.8 Hz, 1H), 5.74 (s, 2H), 3.96 (s, 2H); MS ESI (m/z) 426 $(M+1)^+$.

Example 3: Preparation of Compound XIII

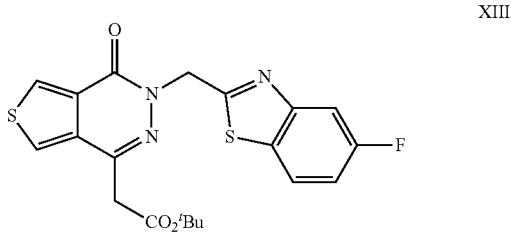 [SMILES: CC(C)(C)OC(=O)Cc1nn(Cc2nc3cc(F)ccc3s2)c(=O)c2cscc12]

Compound XIII, shown above, was prepared as follows: The preparation described for Compound XI was repeated except that 2-(bromomethyl)-5-fluorobenzo[d]thiazole was the reagent employed in place of Compound I-S using the same molar proportions as before. In this case, the final product obtained was tert-butyl 2-(3-((5-fluorobenzo[d]thiazol-2-yl)methyl)-4-oxo-3,4-dihydrothieno[3,4-d]pyridazin-1-yl)acetate (Compound XIII) that was carried on crude after filtering over a plug of silica washing with 2:1 (v/v) hexanes:ethyl acetate Example 4: Preparation of Compound XIV

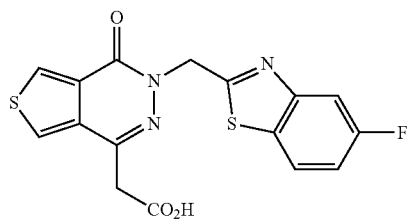

XIV

Compound XIV, shown above, was prepared as follows: The preparation described for Compound XII was repeated except that Compound XIII was the starting material employed in place of Compound XI. In this case, the final product obtained was 2-(3-((5-fluorobenzo[d]thiazol-2-yl)methyl)-4-oxo-3,4-dihydrothieno[3,4-d]pyridazin-1-yl)acetic acid (Compound XIV) in 25% yield: m.p.=172-173° C. (not recrystallized); $^1$H NMR (CDCl$_3$, 400 MHz): $\delta_{ppm}$ 8.47 (d, J=3.2 Hz, 1H), 7.85 (d, J=3.2 Hz, 1H), 7.75-7.69 (m, 2H), 7.13 (dt, J=8.8, 2.8 Hz, 1H), 5.72 (s, 2H), 3.93 (s, 2H); ESI (m/z) 376 (M+H)$^+$.

Example 5: Preparation of Compound XV

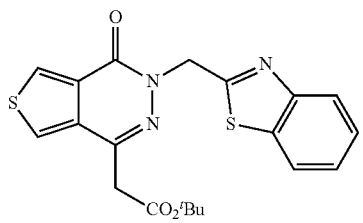

XV

Compound XV, shown above, was prepared as follows: The preparation described for Compound XI was repeated except that 2-(bromomethyl)benzo[d]thiazole was the reagent employed in place of Compound I-S using the same molar proportions as before. In this case, the final product obtained was tert-butyl 2-(3-(benzo[d]thiazol-2-ylmethyl)-4-oxo-3,4-dihydrothieno[3,4-d]pyridazin-1-yl)acetate (Compound XV) that was carried on crude after filtering over a plug of silica washing with 3:1 (v/v) hexanes:ethyl acetate.

Example 6: Preparation of Compound XVI

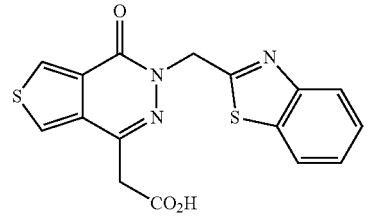

XVI

Compound XVI, shown above, was prepared as follows: The preparation described for Compound XII was repeated except that Compound XV was the starting material employed in place of Compound XI. In this case, the final product obtained was 2-(3-(benzo[d]thiazol-2-ylmethyl)-4-oxo-3,4-dihydrothieno[3,4-d]pyridazin-1-yl)acetic acid (Compound XVI) in 7% yield:: m.p.=172-173° C. (not recrystallized); $^1$H NMR (acetone, 400 MHz): $\delta_{ppm}$ 8.58 (d, J=2.8 Hz, 1H), 8.30 (d, J=2.8 Hz, 1H), 7.99-7.94 (m, 2H), 7.49 (t, J=8.0 Hz, 1H), 7.41 (t, J=8.0 Hz, 1H), 5.68 (s, 2H), 3.94 (s, 2H); ESI (m/z) 358 (M+H)$^+$.

Example 7: Preparation of Compound XVII

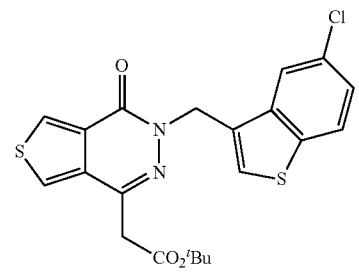

XVII

Compound XVII, shown above, was prepared as follows: The preparation described for Compound XI was repeated except that 3-(bromomethyl)-5-chlorobenzo[b]thiophene was the reagent employed in place of Compound I-S using the same molar proportions as before. In this case, the final product obtained was tert-butyl 2-(3-((5-chlorobenzo[b]thiophen-3-yl)methyl)-4-oxo-3,4-dihydrothieno[3,4-d]pyridazin-1-yl)acetate (Compound XVII). The obtained product was purified via flash column chromatography over silica gel (monitored by thin layer chromatography) and eluted with 3:1 (v/v) hexanes:ethyl acetate. Evaporation of the collected fractions yielded 18% yield of Compound XVII: $^1$H NMR (CDCl$_3$, 400 MHz): $\delta_{ppm}$ 8.38 (d, J=3.2 Hz, 1H), 8.19 (d, J=1.2 Hz, 1H), 7.75 (d, J=3.2 Hz, 1H), 7.72 (d, J=8.8 Hz, 1H), 7.58 (s, 1H), 7.30-7.27 (m, 1H), 5.48 (s, 2H), 3.76 (s, 2H), 1.40 (s, 9H); ESI (m/z) 447 (M+H)$^+$.

Example 8: Preparation of Compound XVIII

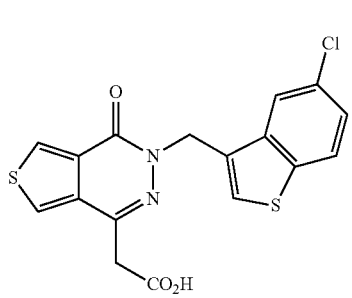

XVIII

Compound XVIII, shown above, was prepared as follows: The preparation described for Compound XII was repeated except that Compound XVII was the starting material employed in place of Compound XI. In this case, the final product obtained was 2-(3-((5-chlorobenzo[b]thiophen-3-yl)methyl)-4-oxo-3,4-dihydrothieno[3,4-d]pyridazin-1-yl)acetic acid (Compound XVIII) in 25% yield:: $^1$H NMR (acetone, 400 MHz): $\delta_{ppm}$ 8.53 (d, J=2.8 Hz, 1H), 8.27 (d, J=2.0 Hz, 1H), 8.23 (d, J=2.8 Hz, 1H), 7.95 (d, J=8.8 Hz, 1H), 7.75 (s, 1H), 7.37 (dd, J=8.8, 2.0 Hz, 1H), 5.51 (s, 2H), 3.92 (s, 2H); ESI (m/z) 391 (M+H)+, 389 (M–H)−.

Example 9: Preparation of Compound XIX

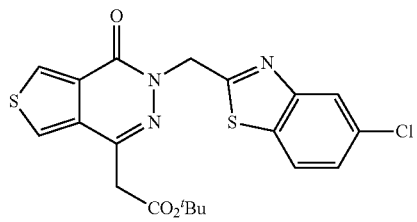

XIX

Compound XIX, shown above, was prepared as follows: The preparation described for Compound XI was repeated except that 5-chloro-2-(chloromethyl)benzo[d]thiazole was the reagent employed in place of Compound I-S using the same molar proportions as before. In this case, the final product obtained was tert-butyl 2-(3-((5-chlorobenzo[d]thiazol-2-yl)methyl)-4-oxo-3,4-dihydrothieno[3,4-d]pyridazin-1-yl)acetate (Compound XIX). The obtained product was purified via flash column chromatography over silica gel (monitored by thin layer chromatography) and eluted with 4:1 (v/v) hexanes:ethyl acetate. Evaporation of the collected fractions yielded 47% yield of Compound XIX: $^1$H NMR (CDCl$_3$, 400 MHz): $\delta_{ppm}$ 8.44 (d, J=3.2 Hz, 1H), 8.00 (s, 1H), 7.82 (d, J=3.2 Hz, 1H), 7.70 (d, J=8.4 Hz, 1H), 7.33 (d, J=8.4 Hz, 1H), 5.72 (s, 2H), 3.77 (s, 2H), 1.40 (s, 9H); ESI (m/z) 448 (M+H)+.

Example 10: Preparation of Compound XX

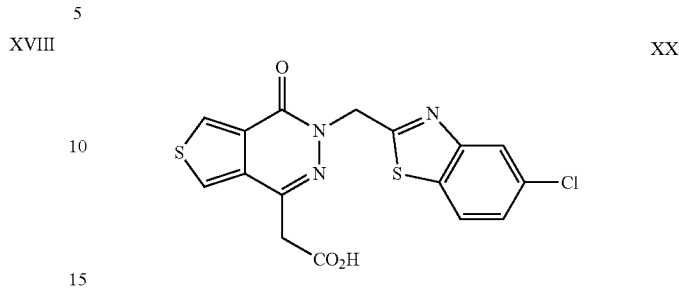

XX

Compound XX, shown above, was prepared as follows: The preparation described for Compound XII was repeated except that Compound XIX was the starting material employed in place of Compound XI. In this case, the final product obtained was 2-(3-((5-chlorobenzo[d]thiazol-2-yl)methyl)-4-oxo-3,4-dihydrothieno[3,4-d]pyridazin-1-yl)acetic acid (Compound XX) in 61% yield: m.p.=184-185° C. (not recrystallized); $^1$H NMR (acetone, 400 MHz): $\delta_{ppm}$ 8.59 (d, J=2.8 Hz, 1H), 8.32 (d, J=2.8 Hz, 1H), 8.03-7.99 (m, 2H), 7.45 (d, J=8.8 Hz, 1H), 5.69 (s, 2H), 3.95 (s, 2H); ESI (m/z) 392 (M+H)+.

Example 11: Preparation of Compound XXI

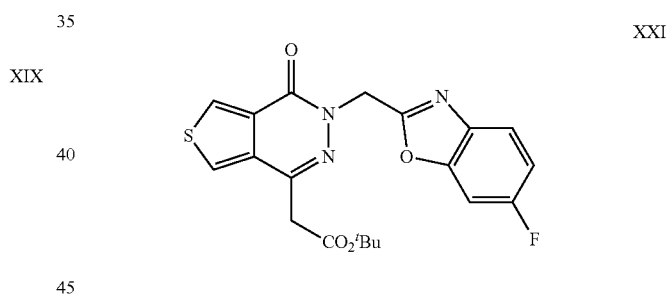

XXI

Compound XXI, shown above, was prepared as follows: The preparation described for Compound XI was repeated except that 2-(chloromethyl)-6-fluorobenzo[d]oxazole was the reagent employed in place of Compound I-S using the same molar proportions as before. In this case, the final product obtained was tert-butyl 2-(3-((6-fluorobenzo[d]oxazol-2-yl)methyl)-4-oxo-3,4-dihydrothieno[3,4-d]pyridazin-1-yl)acetate (Compound XXI). The obtained product was purified via flash column chromatography over silica gel (monitored by thin layer chromatography) and eluted with 4:1 (v/v) hexanes:ethyl acetate. Evaporation of the collected fractions yielded 30% yield of Compound XXI: $^1$H NMR (CDCl$_3$, 400 MHz): $\delta_{ppm}$ 8.44 (d, J=3.2 Hz, 1H), 7.81 (d, J=3.2 Hz, 1H), 7.60 (dd, J=8.8, 4.8 Hz, 1H), 7.19 (dd, J=7.6, 2.0 Hz, 1H), 7.05 (dt, J=8.8, 2.0 Hz, 1H), 5.58 (s, 2H), 3.75 (s, 2H), 1.40 (s, 9H); ESI (m/z) 416 (M+H)+.

Example 12: Preparation of Compound XXII

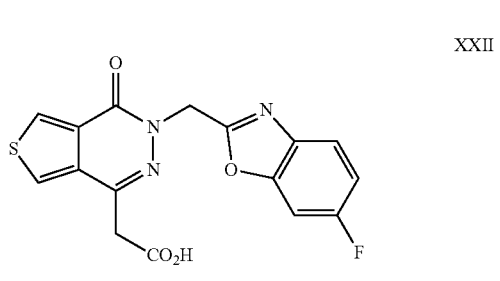 [SMILES: O=C(O)Cc1nn(Cc2nc3ccc(F)cc3o2)c(=O)c2cscc12]

Compound XXII, shown above, was prepared as follows: The preparation described for Compound XII was repeated except that Compound XXI was the starting material employed in place of Compound XI. In this case, the final product obtained was 2-(3-((6-fluorobenzo[d]oxazol-2-yl)methyl)-4-oxo-3,4-dihydrothieno[3,4-d]pyridazin-1-yl)acetic acid (Compound XXII) in 40% yield:: $^1$H NMR (acetone, 400 MHz): $\delta_{ppm}$ 8.57 (d, J=3.2 Hz, 1H), 8.30 (d, J=3.2 Hz, 1H), 7.65 (dd, J=8.8, 5.2 Hz, 1H), 7.45 (dd, J=8.0, 2.4 Hz, 1H), 7.17 (dt, J=8.8, 2.4 Hz, 1H), 5.57 (s, 2H), 3.91 (s, 2H); ESI (m/z) 360 (M+H)$^+$.

Example 13: Preparation of Compound XXIII

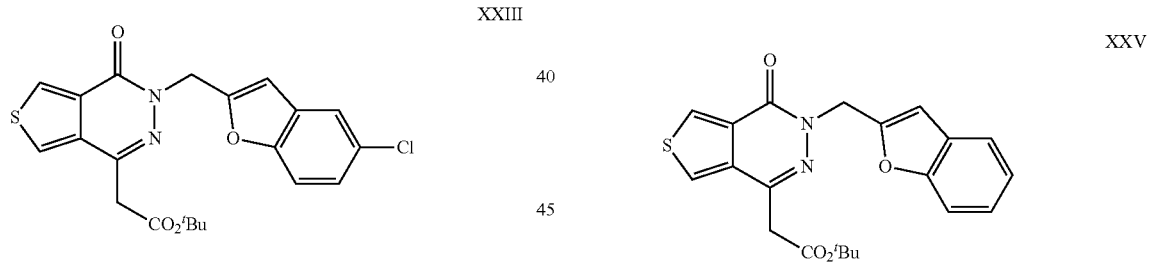

Compound XXIII, shown above, was prepared as follows: The preparation described for Compound XI was repeated except that 5-chloro-2-(chloromethyl)benzofuran was the reagent employed in place of Compound I-S using the same molar proportions as before. In this case, the final product obtained was tert-butyl 2-(3-((5-chlorobenzofuran-2-yl)methyl)-4-oxo-3,4-dihydrothieno[3,4-d]pyridazin-1-yl)acetate (Compound XXIII). The obtained product was purified via flash column chromatography over silica gel (monitored by thin layer chromatography) and eluted with 2:1 (v/v) hexanes:ethyl acetate. Evaporation of the collected fractions yielded 33% yield of Compound XXIII: m.p.=117-118° C. (not recrystallized); $^1$H NMR (CDCl$_3$, 400 MHz): $\delta_{ppm}$ 8.40 (d, J=3.2 Hz, 1H), 7.78 (d, J=3.2 Hz, 1H), 7.45 (d, J=2.4 Hz, 1H), 7.33 (d, J=8.4 Hz, 1H), 7.17 (dd, J=8.4, 2.4 Hz, 1H), 6.65 (s, 1H), 5.44 (s, 2H), 3.76 (s, 2H), 1.41 (s, 9H); ESI (m/z) 431 (M+H)$^+$.

Example 14: Preparation of Compound XXIV

Compound XXIV, shown above, was prepared as follows: The preparation described for Compound XII was repeated except that Compound XXIII was the starting material employed in place of Compound XI. In this case, the final product obtained was 2-(3-((5-chlorobenzofuran-2-yl)methyl)-4-oxo-3,4-dihydrothieno[3,4-d]pyridazin-1-yl)acetic acid (Compound XXIV) in 54% yield: m.p.=154-155° C. (not recrystallized); $^1$H NMR (acetone, 400 MHz): $\delta_{ppm}$ 8.54 (d, J=3.2 Hz, 1H), 8.26 (d, J=3.2 Hz, 1H), 7.60 (d, J=2.0 Hz, 1H), 7.47 (d, J=8.8 Hz, 1H), 7.26 (dd, J=8.8, 2.0 Hz, 1H), 6.77 (s, 1H), 5.44 (s, 2H), 3.91 (s, 2H); ESI (m/z) 375 (M+H)$^+$.

Example 15: Preparation of Compound XXV

Compound XXV, shown above, was prepared as follows: The preparation described for Compound XI was repeated except that 2-(chloromethyl)benzofuran was the reagent employed in place of Compound I-S using the same molar proportions as before. In this case, the final product obtained was tert-butyl 2-(3-(benzofuran-2-ylmethyl)-4-oxo-3,4-dihydrothieno[3,4-d]pyridazin-1-yl)acetate (Compound XXV). The obtained product was purified via flash column chromatography over silica gel (monitored by thin layer chromatography) and eluted with 2:1 (v/v) hexanes:ethyl acetate. Evaporation of the collected fractions yielded 44% yield of Compound XXV: $^1$H NMR (CDCl$_3$, 400 MHz): $\delta_{ppm}$ 8.40 (d, J=3.2 Hz, 1H), 7.76 (d, J=3.2 Hz, 1H), 7.48 (d, J=7.6 Hz, 1H), 7.41 (d, J=8.0, 1H), 7.22 (t, J=8.0 Hz, 1H), 7.17 (t, J=7.6 Hz, 1H), 6.70 (s, 1H), 5.45 (s, 2H), 3.76 (s, 2H), 1.40 (s, 9H); ESI (m/z) 397 (M+H)$^+$.

Example 16: Preparation of Compound XXVI

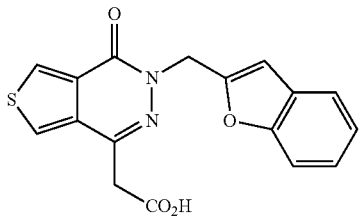

Compound XXVI, shown above, was prepared as follows: The preparation described for Compound XII was repeated except that Compound XXV was the starting material employed in place of Compound XI. In this case, the final product obtained was 2-(3-(benzofuran-2-ylmethyl)-4-oxo-3,4-dihydrothieno[3,4-d]pyridazin-1-yl)acetic acid (Compound XXVI) in 28% yield: m.p.=158-159° C. (not recrystallized); $^1$H NMR (acetone, 400 MHz): $\delta_{ppm}$ 8.54 (d, J=3.2 Hz, 1H), 8.26 (d, J=3.2 Hz, 1H), 7.56 (d, J=7.6 Hz, 1H), 7.45 (d, J=8.4 Hz, 1H), 7.26 (t, J=8.4 Hz, 1H), 7.20 (t, J=7.6 Hz, 1H), 6.76 (s, 1H), 5.44 (s, 2H), 3.91 (s, 2H); ESI (m/z) 341 (M+H)$^+$.

Example 17: Physical, Chemical, and Biological Assay Methods and Results

Characterization of Aldose Reductase Inhibitor Compounds:

The compounds were synthesized as summarized previously and were characterized in terms of physical characteristics (solubility and Log D) as well as biochemically in terms of ability to inhibit Aldose Reductase enzymatic activity in vitro. Methods for these assays and results are summarized below.

Equilibrium Solubility in Phosphate Buffer, pH 7.4:

The equilibrium solubility of test articles was measured in pH 7.4 aqueous buffers. The pH 7.4 buffer was prepared by combining 50 mL of 0.2 M $KH_2PO_4$ with 150 mL of $H_2O$, and then adjusting to pH 7.4 with 10 N NaOH. At least 1 mg of powder for each test article was combined with 1 mL of buffer to make a ≥1 mg/mL mixture. These samples were shaken on a Thermomixer® overnight at room temperature. The samples were then centrifuged for 10 minutes at 10,000 rpm. The supernatant was sampled and diluted in duplicate 10-fold, 100-fold, and 10,000-fold into a mixture of 1:1 buffer:acetonitrile (ACN) prior to analysis. All samples were assayed by LC-MS/MS using electrospray ionization against standards prepared in a mixture of 1:1 assay buffer:ACN. Standard concentrations ranged from 1.0 μM to 1.0 nM.

Octanol/Buffer Partition Coefficient (Log D) at pH 7.4:

The octanol/buffer partition coefficient of three test articles was measured at pH 7.4. The pH 7.4 buffer was prepared by combining 50 mL of 0.2 M solution of $KH_2PO_4$ with 150 mL of $dH_2O$, and then adjusting to pH 7.4 with 10 N NaOH. In a single incubation, 15 μL of a 10 mM DMSO solution of each test article (100 μM) was added to test tubes which contained 0.75 mL of octanol and 0.75 mL of pH 7.4 phosphate buffer. Testosterone was also introduced to each tube as an internal control, also at a dosing concentration of 100 μM. These samples were gently mixed on a benchtop rotator for 1 hour at room temperature. The tubes were then removed from the rotator and the aqueous and organic phases were allowed to separate for 1 hour. An aliquot of the organic layer was taken and diluted 200-fold into a mixture of 1:1 buffer:acetonitrile (ACN). An aliquot of the aqueous layer was taken and diluted 2-fold, 10-fold, and 200-fold into a mixture of 1:1 buffer:ACN. All samples were assayed by LC-MS/MS using electrospray ionization. Testsosterone was utilized as a positive control (with a published/known Log D of 3.0-3.4).

Aldose Reductase Enzymatic Inhibition:

All compounds and Zopolrestat were tested individually in a micro plate assay for AR inhibition using D-glyceraldehyde and NADPH as substrate and the absorbance changes at 340 nm was monitored. % Inhibition was calculated for ARIs at concentration ranging 0.1 nm to 10 uM. The enzymatic inhibition assay was performed as described in WO 2012/009553, which is hereby incorporated by reference in its entirety.

TABLE 1

Physical, Chemical, and Biological Assay Results:

| Compound | Structure | Mol. Wt. (AMU) | Solubility (mg/mL) | LogD | Aldose Reductase Inhibition (IC50) |
|---|---|---|---|---|---|
| XIV | 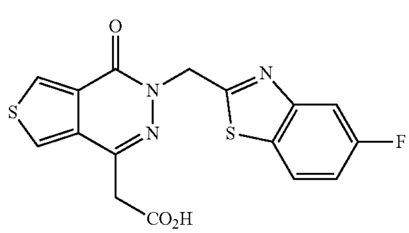 [SMILES: O=C(O)Cc1nn(Cc2nc3cc(F)ccc3s2)c(=O)c2cscc12] | 375 | 0.65 | −0.87 | 60 nM |

TABLE 1-continued

Physical, Chemical, and Biological Assay Results:

| Compound | Structure | Mol. Wt. (AMU) | Solubility (mg/mL) | LogD | Aldose Reductase Inhibition (IC50) |
|---|---|---|---|---|---|
| VI | 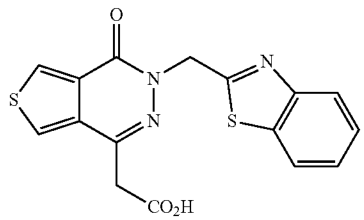 [SMILES: O=C(O)Cc1nn(Cc2nc3ccccc3s2)c(=O)c2cscc12] | 357 | 0.81 | −1.01 | 190 nM |
| XX | 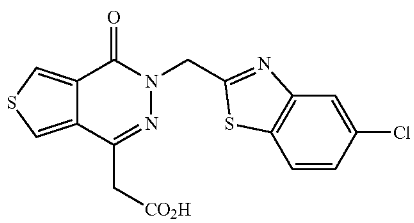 [SMILES: O=C(O)Cc1nn(Cc2nc3cc(Cl)ccc3s2)c(=O)c2cscc12] | 391 | 0.59 | −0.35 | 35 nM |
| XII | 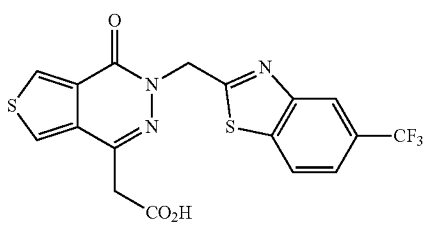 [SMILES: O=C(O)Cc1nn(Cc2nc3cc(C(F)(F)F)ccc3s2)c(=O)c2cscc12] | 425 | 0.97 | −0.09 | 0.1 nM |
| XXVI | 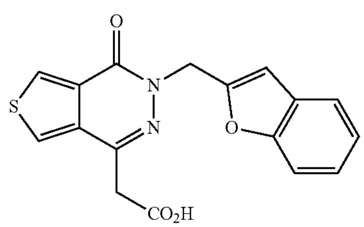 | 340 | 0.79 | −0.86 | 57 nM |
| XIV | 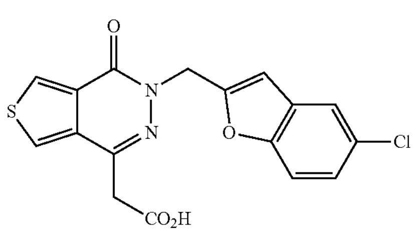 [SMILES: O=C(O)Cc1nn(Cc2cc3cc(Cl)ccc3o2)c(=O)c2cscc12] | 374 | 0.76 | −0.01 | 64 nM |

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

What is claimed is:

1. A compound of Formula (I)

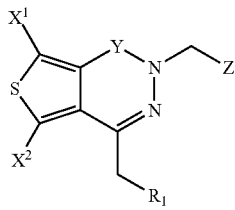

wherein,
$R^1$ is $CO_2R^2$;
$R^2$ is H, $(C_1-C_6)$-alkyl, $(C_1-C_6)$-hydroxyalkyl, or $(C_1-C_6)$-aminoalkyl;
$X^1$ is H or halogen;
$X^2$ is H or halogen;
Y is a bond, C=O, C=S, C=NH, or C=N$(C_1-C_4)$-alkyl;
Z is

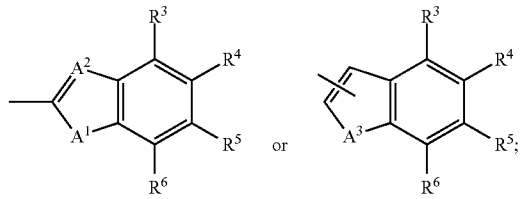

$A^1$ is $NR^7$, O, S or $CH_2$;
$A^2$ is N or CH;
$A^3$ is $NR^7$, O, or S;
$R^3$ through $R^6$ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkyl sulfonyl; and
$R^7$ is hydrogen, $C_1-C_4$ alkyl, or C(O)O—$(C_1-C_4)$-alkyl; or a pharmaceutically acceptable salt or solvate thereof.

2. The compound of claim 1, wherein
$R^2$ is hydrogen or $(C_1-C_6)$-alkyl;
Y is C=O;
$A^1$ is $NR^7$, O, or S;
$A^2$ is N;
$A^3$ is O, or S; and
$R^3$ through $R^6$ are independently hydrogen, halogen, cyano, acyl, haloalkyl, haloalkoxy, haloalkylthio, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl;
or a pharmaceutically acceptable salt or solvate thereof.

3. The compound of claim 1, wherein Z is

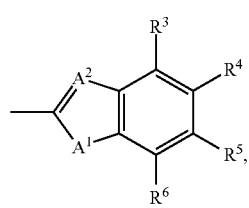

or a pharmaceutically acceptable salt or solvate thereof.

4. The compound of claim 3, wherein
$R^2$ is hydrogen or $(C_1-C_6)$-alkyl;
Y is C=O;
$A^1$ is $NR^7$, O, or S;
$A^2$ is N;
$R^3$ through $R^6$ are independently hydrogen, halogen, cyano, acyl, haloalkyl, haloalkoxy, haloalkylthio, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl; and
$R^7$ is hydrogen, $C_1-C_4$ alkyl, or C(O)O—$(C_1-C_4)$-alkyl; or a pharmaceutically acceptable salt or solvate thereof.

5. The compound of claim 3, wherein
$R^2$ is hydrogen or $(C_1-C_6)$-alkyl;
$X^1$ is H;
$X^2$ is H;
Y is C=O;
$A^1$ is S;
$A^2$ is N; and
$R^3$ through $R^6$ are independently hydrogen, halogen, or haloalkyl, or a pharmaceutically acceptable salt or solvate thereof.

6. The compound of claim 1, wherein Z is

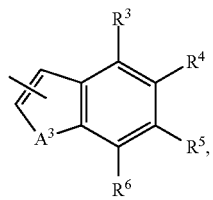

or a pharmaceutically acceptable salt or solvate thereof.

7. The compound of claim 6, wherein
$R^2$ is hydrogen or $(C_1-C_6)$-alkyl;
Y is C=O;
$R^3$ through $R^6$ are independently hydrogen, halogen, cyano, acyl, haloalkyl, haloalkoxy, haloalkylthio, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl; and
$R^7$ is hydrogen, $C_1-C_4$ alkyl, or C(O)O—$(C_1-C_4)$-alkyl; or a pharmaceutically acceptable salt or solvate thereof.

8. The compound of claim 1, wherein
$R^2$ is hydrogen;
$X^1$ is Cl;
$X^2$ is Cl;
Y is C=O;
$R^3$ through $R^6$ are independently hydrogen, halogen, or haloalkyl; and
$R^7$ is hydrogen, $(C_1-C_4)$-alkyl, or C(O)O-tert-butyl; or a pharmaceutically acceptable salt or solvate thereof.

9. The compound of claim 1, wherein
$R^2$ is hydrogen;
$X^1$ is Cl;
$X^2$ is Cl;
Y is C=O;
$A^3$ is is $NR^7$, O or S; and
$R^3$, $R^5$, and $R^6$ are hydrogen;
$R^4$ is hydrogen or halogen; and
$R^7$ is hydrogen, $(C_1-C_4)$-alkyl, or C(O)O-tert-butyl; or a pharmaceutically acceptable salt or solvate thereof.

10. The compound of claim 1, selected from the group consisting of:

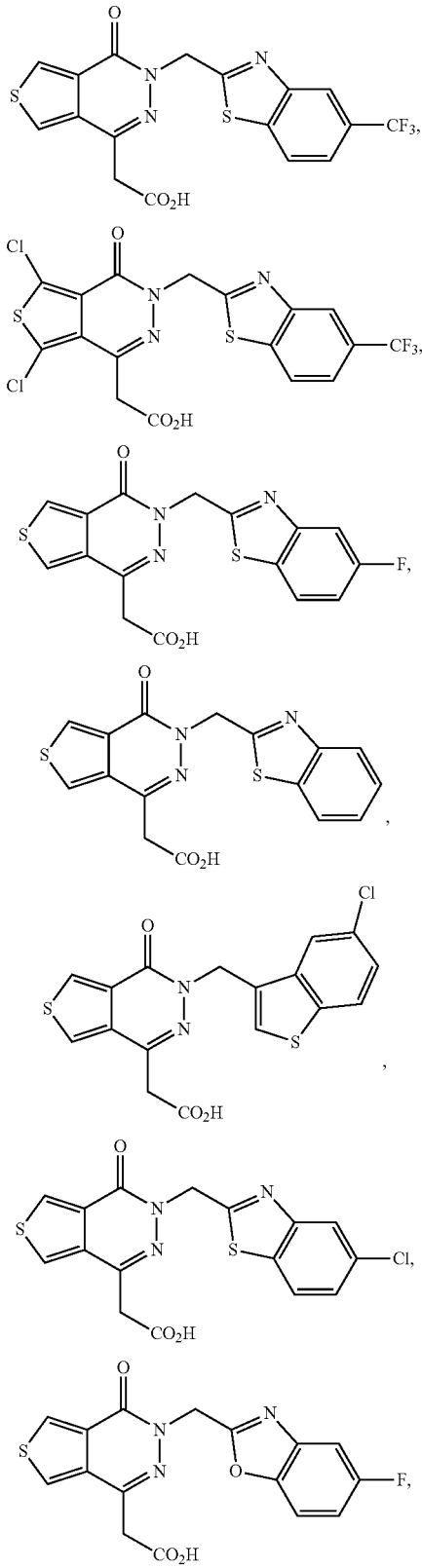

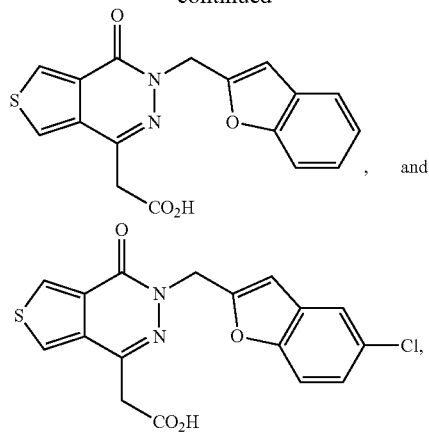

or a pharmaceutically acceptable salt or hydrate of any one of the foregoing.

11. The compound of claim 1, wherein the compound is a pharmaceutically acceptable salt and the counter ion is selected from the group consisting of: sodium, lithium, potassium, calcium, magnesium, zinc, ammonium, and tetrafluoroborate.

12. The compound of claim 1, wherein the compound is a pharmaceutically acceptable salt and the counter ion is selected from the group consisting of:

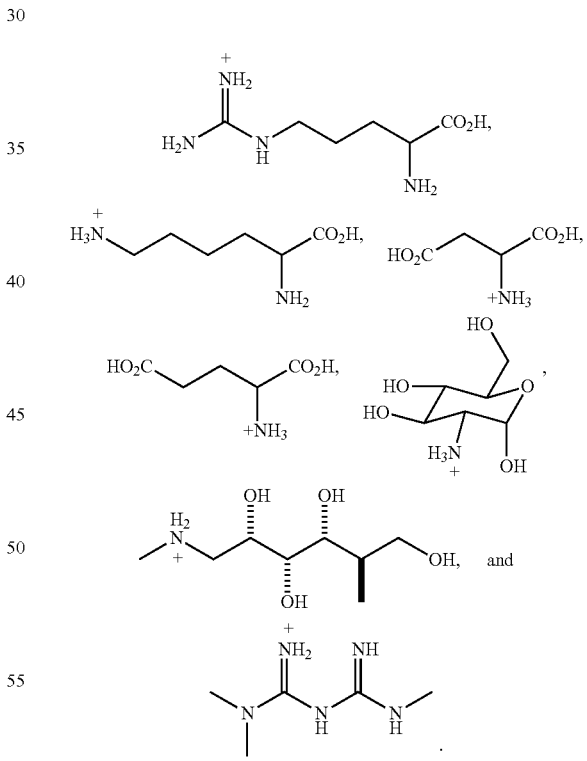

13. A pharmaceutical composition comprising a compound of claim 1 and a pharmaceutically acceptable carrier.

14. A method of inhibiting aldose reductase activity in a subject comprising administering a therapeutically effective amount of the compound of claim 1 to a subject in need thereof.

15. The method of claim 14, wherein the subject is diabetic.

16. The method of claim 14, wherein the subject is a human.

17. A method of treating a disorder in a subject comprising administration of a therapeutically effective amount of the compound of claim 1 to a subject in need thereof, wherein the disorder is selected from the group consisting of atherosclerosis, diabetic nephropathy, diabetic neuropathy, diabetic retinopathy, cardiovascular disease, peripheral vascular disease, angiogenesis disorder, tissue damage and diabetic cardiomyopathy.

18. The method of claim 17, wherein the disorder is atherosclerosis, diabetic nephropathy, diabetic neuropathy, diabetic retinopathy, or diabetic cardiomyopathy.

19. A method to treat a skin disorder or promote healthy aging of skin, comprising applying a therapeutically effective amount of the compound of claim 1 to the skin of a human subject in need thereof.

20. A method of treating a subject with evolving myocardial infarction comprising administering to a subject in need thereof a therapeutically effective amount of the compound of claim 1.

* * * * *